United States Patent
Sapra

(10) Patent No.: US 7,671,067 B2
(45) Date of Patent: Mar. 2, 2010

(54) TREATMENT OF NON-HODGKIN'S LYMPHOMAS WITH MULTI-ARM POLYMERIC CONJUGATES OF 7-ETHYL-10-HYDROXYCAMTOTHECIN

(75) Inventor: Puja Sapra, Edison, NJ (US)

(73) Assignee: Enzon Pharmaceuticals, Inc., Bridgewater, NJ (US)

( * ) Notice: Subject to any disclaimer, the term of this patent is extended or adjusted under 35 U.S.C. 154(b) by 174 days.

(21) Appl. No.: 11/840,773

(22) Filed: Aug. 17, 2007

(65) Prior Publication Data

US 2008/0058364 A1 Mar. 6, 2008

Related U.S. Application Data

(63) Continuation-in-part of application No. 11/704,607, filed on Feb. 9, 2007, now Pat. No. 7,462,627.

(60) Provisional application No. 60/772,464, filed on Feb. 9, 2006, provisional application No. 60/804,391, filed on Jun. 9, 2006, provisional application No. 60/844,938, filed on Sep. 15, 2006, provisional application No. 60/864,516, filed on Nov. 6, 2006.

(51) Int. Cl.
A61K 31/4745 (2006.01)
C07D 491/22 (2006.01)

(52) U.S. Cl. ......................... 514/283; 546/48

(58) Field of Classification Search ............... 514/283; 546/48
See application file for complete search history.

(56) References Cited

U.S. PATENT DOCUMENTS

| | | | |
|---|---|---|---|
| 4,473,692 A | 9/1984 | Miyasaka et al. |
| 5,614,549 A | 3/1997 | Greenwald et al. |
| 5,648,506 A | 7/1997 | Desai et al. |
| 5,681,567 A | 10/1997 | Martinez et al. |
| 5,736,156 A | 4/1998 | Burke |
| 5,840,900 A | 11/1998 | Greenwald et al. |
| 5,840,973 A | 11/1998 | Yasukohchi et al. |
| 5,859,022 A | 1/1999 | Hausheer et al. |
| 5,880,131 A | 3/1999 | Greenwald et al. |
| 5,902,588 A | 5/1999 | Greenwald et al. |
| 5,948,155 A | 9/1999 | Yui et al. |
| 5,965,566 A | 10/1999 | Greenwald et al. |
| 6,011,042 A | 1/2000 | Greenwald et al. |
| 6,111,107 A | 8/2000 | Greenwald et al. |
| 6,121,451 A | 9/2000 | Henegar et al. |
| 6,127,355 A | 10/2000 | Greenwald et al. |
| 6,153,655 A | 11/2000 | Martinez et al. |
| 6,177,087 B1 | 1/2001 | Greenwald et al. |
| 6,194,580 B1 | 2/2001 | Greenwald et al. |
| 6,395,266 B1 | 5/2002 | Martinez et al. |
| 6,403,569 B1 | 6/2002 | Achterrath |
| 6,608,076 B1 | 8/2003 | Greenwald et al. |
| 6,638,499 B2 | 10/2003 | Martinez et al. |
| 6,649,778 B1 | 11/2003 | Zhao et al. |
| 6,723,338 B1 | 4/2004 | Sarris et al. |
| 6,756,037 B2 | 6/2004 | Greenwald et al. |
| 6,875,841 B2 | 4/2005 | Sakanoue et al. |
| 6,897,200 B1 | 5/2005 | Burke et al. |
| 7,462,627 B2 * | 12/2008 | Zhao et al. ............... 514/283 |
| 2001/0041172 A1 | 11/2001 | Bentley et al. |
| 2002/0182172 A1 | 12/2002 | Bentley et al. |
| 2003/0105275 A1 | 6/2003 | Bentley et al. |
| 2004/0009229 A1 | 1/2004 | Unger et al. |
| 2004/0058981 A1 | 3/2004 | Lai et al. |
| 2004/0077595 A1 | 4/2004 | Cheng et al. |
| 2004/0247624 A1 | 12/2004 | Unger et al. |
| 2005/0112088 A1 | 5/2005 | Zhao et al. |
| 2005/0226843 A1 | 10/2005 | Bentley et al. |
| 2006/0135527 A1 | 6/2006 | Houghton et al. |
| 2008/0193408 A1 | 8/2008 | Zhao et al. |

FOREIGN PATENT DOCUMENTS

| | | |
|---|---|---|
| EP | 0757049 B1 | 3/1999 |
| WO | WO 199841562 | 9/1998 |
| WO | WO 200064486 | 11/2000 |
| WO | WO 200168066 A3 | 9/2001 |
| WO | WO 200174402 | 10/2001 |
| WO | WO 2002089789 A1 | 11/2002 |
| WO | WO 2003031467 | 4/2003 |
| WO | WO 2003037384 | 5/2003 |
| WO | WO 2003037385 A1 | 5/2003 |
| WO | WO 2004060967 | 7/2004 |
| WO | WO 2007092646 A2 | 8/2007 |

OTHER PUBLICATIONS

International Search Report and Written Opinion dated Aug. 13, 2008 issued in PCT/US07/03808.
Zalipsky et al., Attachment Of Drugs To Polyethylene Glycols, European Polymer Journal, 1983, 19(12): 1177-1183.
Greenwald et al., Poly(ethylene glycol) Conjugated Drugs and Prodrugs: A Comprehensive Review, Critical Review in Therapeutic Drug Carrier Systems, 2000, 17(2): 101-161.
Greenwald, R. B., et al., Camptothecin-20-PEG ester Transport Forms: the Effect of . . . , Bioorganic & Medicinal Chemistry, 6: 551-562, 1998.
Conover, C. D., et al., Camptothecin delivery systems: the utility of amino acid spacers for . . . , Anticancer Drug Design, 14: 499-506, 1999.
Carpino, L. A., et al., New family of base- and nucleophile-sensitive amino-protecting groups. A Michael-acceptor-based deblocking process. Practical utilization of the 1,1-dioxobenzo[b]thiophene-2-ylmethylcarbonyl (Bsmoc) group, Journal of the American Chemical Society, 119:9915-9916, 1997.

(Continued)

Primary Examiner—Charanjit S Aulakh

(57) ABSTRACT

The present invention relates to methods of treatment of non-Hodgkin's lymphomas. The present invention includes administering polymeric prodrugs of 7-ethyl-10-hydroxy-camptothecin to patients in need thereof.

20 Claims, 6 Drawing Sheets

OTHER PUBLICATIONS

Chabot, G. G., Clinical pharmacokinetics or irinotecan, Clinical Pharmacokinet, 33: 245-259, 1997.

Choe, Y. H., et al., Anticancer drug delivery systems: N4-acyl-poly(ethyleneglycol) prodrugs of ara-C. I. Efficacy in solid tumors, Journal of Controlled Release, 79: 41-53, 2002.

Conover, C. D., et al., Campothecin delivery systems: enhanced efficacy and tumor accumulation of campotothecin following its conjugation to polyethylene glycol via a glycine linker, Cancer Chemotherapy Pharmacology, 407-414, 1998.

Duncan, R., Polymer conjugates as anticancer nanomedicines, Nature Reviews: Cancer, 6: 688-701, 2006.

Garcia-Carbonero, R., et al., Current perspectives on the clinical experience, pharmacology, and continued development of the camptothecins, Clinical Cancer Research, 8:641-661, 2002.

Gottlieb, J. A., et al., Preliminary pharmacologic and clinical evaluation of camptothecin sodium (NSC-100880), Cancer Chemotherapy Reports, 54: 461-470, 1970.

Greenwald, R. B., et al., Synthesis, isolation, and characterization of 2'-paclitaxel glycinate: an application of the Bsmoc protecting group, Journal of Organic Chemistry, 68: 4894-6, 2003.

Greenwald, R. B., et al., Drug delivery systems. 2. Camptothecin 20-O-poly(ethylene glycol) ester transport forms, Journal of Medicinal Chemistr, 39: 1938-1940, 1996.

Greenwald, R. B., et al., Drug delivery systems: water soluble taxol 2'-poly(ethylene glycol) ester prodrugs-Design and in vivo effectiveness, Journal of Medicinal Chemistry, 39: 424-431, 1996.

Greenwald, R. B., et al., Effective drug delivery by PEGylated drug conjugates, Advanced Drug Delivery Reviews, 55: 217-250, 2003.

Kaneda, N., et al., Metabolism and pharmacokinetics of the camptothecin analogue CPT-11 in the mouse, Cancer Research, 50:1715-1720, 1990.

Kawato, Y., et al., Intracellular roles of SN-38, a metabolite of the camptothecin derivative CPT-11, in the antitumor effect of CPT-11, Cancer Research, 51: 4187-4191, 1991.

Liu, X., et al., Degradation of camptothecin-20(S)-glycinate ester prodrug under physiological conditions, Journal of Pharmaceutical and Biomedical Analysis, 35: 1113-1125, 2004.

Maeda, H., et al., Tumor vascular permeability and the EPR effect in macromolecular therapeutics: a review, Journal of Controlled Release, 65: 271-284, 2000.

Mathijssen, R. H. J., et al., Clinical pharmacokinetics and metabolism of irinotecan (CPT-11), Clinical Cancer Research, 7: 2182-2194, 2001.

Pommier, Y., Topoisomerase I inhibitors: camptothecins and beyond, Nature Reviews: Cancer, 6: 789-802, 2006.

Rowinsky, E. K., et al., A Phase I and pharmacokinetic study of pegylated camptothecin as a 1-hour infusion every 3 weeks in patients with advanced solid malignancies, Journal of Clinical Oncology, 148-157, 2003.

Senter, P. D., et al., Identification and activities of human carboxylesterases for the activation of CPT-11, a clinically approved anticancer drug, Bioconjugate Chemistry, 12: 1074-1080, 2001.

Slatter, J. G., et al., Bioactivation of the anticancer agent CPT-11 to SN 38 by human hepatic microsomal carboxylesterases and the in vitro assessment of potential drug interactions, Drug Metabolism and Disposition, 25: 1157-1164, 1997.

Slatter, J. G., et al., Pharmacokinetics, metabolism, and excretion of irinotecan (CPT-11) following i.v. infusion of [14C]CPT-11 in cancer patients, Drug Metabolism and Disposition, 28: 423-433, 2000.

Smith, N. F., et al., Pharmacogenetics of irinotecan metabolism and transport: an update, Toxicology in Vitro, 20: 163-175, 2006.

Ulukan, H., et al., Camptothecins: a review of their chemotherapeutic potential, Drugs, 62: 2039-57, 2002.

Zhang, J. A., et al., Development and characterization of a novel liposome-based formulation of SN-38, International Journal of Pharmaceutics, 270: 93-107, 2004.

Zhao, H., et al., 20-O-acylcamptothecin derivatives: evidence for lactone stabilization, Journal of Organic Chemistry, 65: 4601-4606, 2000.

International Search Report and Written Opinion issued in PCT/US07/76241 and dated Aug. 8, 2008.

Office Action issued in U.S. Appl. No. 12/274,474 and dated May 8, 2009.

Office Action issued in U.S. Appl. No. 12/028,378 and dated Feb. 23, 2009.

* cited by examiner

TREATMENT OF NON-HODGKIN'S LYMPHOMAS WITH MULTI-ARM POLYMERIC CONJUGATES OF 7-ETHYL-10-HYDROXYCAMTOTHECIN

CROSS-REFERENCE TO RELATED APPLICATION

This application is a Continuation-in-Part of U.S. patent application Ser. No. 11/704,607 filed Feb. 9, 2007, now U.S. Pat. No. 7,462,627 which in turn claims the benefit of priority from U.S. Provisional Patent Application Ser. Nos. 60/772,464 filed Feb. 9, 2006, 60/804,391 filed Jun. 9, 2006, 60/844,938 filed Sep. 15, 2006 and 60/864,516 filed Nov. 6, 2006, the contents of each of which are incorporated herein by reference.

FIELD OF INVENTION

The present invention relates to methods of treating lymphomas with polymeric prodrugs of 7-ethyl-10-hydroxy-camptothecin. In particular, the invention relates to methods of treating non-Hodgkin's lymphomas with polyethylene glycol conjugates of 7-ethyl-10-hydroxycamptothecin.

BACKGROUND OF INVENTION

Non-Hodgkin lymphomas (NHL) are a group of cancers associated with the immune system such as lymphocytes. NHL may develop in any organs associated with lymphatic system such as spleen, lymph nodes or tonsils. NHL can occur at any age and are often marked by enlarged lymph nodes, fever, and weight loss. NHL is generally grouped into aggressive (fast-growing) and indolent (slow-growing) types. NHL is also classified as either B-cell or T-cell NHL. B-cell NHL includes Burkitt's lymphoma, diffuse large B-cell lymphoma, follicular lymphoma, immunoblastic large cell lymphoma, precursor B-lymphoblastic lymphoma, and mantle cell lymphoma. T-cell NHL includes mycosis fungoides, anaplastic large cell lymphoma, and precursor T-lymphoblastic lymphoma. Lymphomas related to lymphoproliferative disorders following bone marrow or stem cell transplantation are usually B-cell NHL. Prognosis and treatment depend on the stage and type of disease.

Over the years, several methods of treating patients with non-Hodgkin's lymphomas have been proposed. Some attempts include therapies based on CPT-11 also known as Irinotecan (CPT-11, Camptosar®). The results associated with these attempts have been thought of as being unsuccessful. The present invention provides an alternative for such treatment.

SUMMARY OF INVENTION

In one aspect of the present invention, there are provided methods of treating patients having non-Hodkins's lymphomas. The treatment includes administering an effective amount of a compound of Formula (I) to a patient in need thereof.

In accordance with this aspect of the invention, compounds of Formula (I) used include

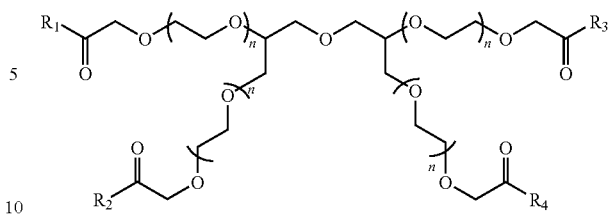

wherein
$R_1$, $R_2$, $R_3$ and $R_4$ are independently OH or $(L)_m$-D;
L is a bifunctional linker;
D is

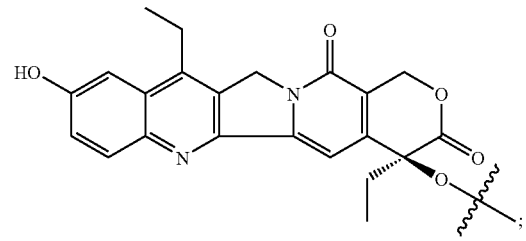

m is 0 or a positive integer; and
n is a positive integer;

provided that $R_1$, $R_2$, $R_3$ and $R_4$ are not all OH.

In certain preferred aspects of the invention, n is from about 28 to about 341, and is preferably about 227.

Advantages will be apparent from the following description and drawings.

For purposes of the present invention, the term "residue" shall be understood to mean that portion of a compound, to which it refers, i.e. 7-ethyl-10-hydroxycamptothecin, amino acid, etc. that remains after it has undergone a substitution reaction with another compound.

For purposes of the present invention, the term "polymeric containing residue" or "PEG residue" shall each be understood to mean that portion of the polymer or PEG which remains after it has undergone a reaction with 7-ethyl-10-hydroxycamptothecin-containing compounds.

For purposes of the present invention, the term "alkyl" shall be understood to include straight, branched, substituted, e.g. halo-, alkoxy-, nitro-, $C_{1-12}$, but preferably $C_{1-4}$ alkyls, $C_{3-8}$ cycloalkyls or substituted cycloalkyls, etc.

For purposes of the present invention, the term "substituted" shall be understood to include adding or replacing one or more atoms contained within a functional group or compound with one or more different atoms.

For purposes of the present invention, substituted alkyls include carboxyalkyls, aminoalkyls, dialkylaminos, hydroxyalkyls and mercaptoalkyls; substituted alkenyls include carboxyalkenyls, arninoalkenyls, dialkenylaminos, hydroxyalkenyls and mercaptoalkenyls; substituted alkynyls include carboxyalkynyls, aminoalkynyls, dialkynylinos, hydroxyalkynyls and mereaptoalkynyls; substituted cycloalkyls include moieties such as 4-chlorocyclohexyl; aryls include moieties such as napthyl; substituted aryls include moieties such as 3-bromo phenyl; aralkyls include moieties such as tolyl; heteroalkyls include moieties such as ethylthiophene; substituted heteroalkyls include moieties such as 3-methoxy-thiophene; alkoxy includes moieties such as methoxy; and phenoxy includes moieties such as 3-nitrophenoxy. Halo shall be understood to include fluoro, chloro, iodo and bromo.

The terms "effective amounts" and "sufficient amounts" for purposes of the present invention shall mean an amount which achieves a desired effect or therapeutic effect as such effect is understood by those of ordinary skill in the art.

DETAILED DESCRIPTION OF INVENTION

Figure 1:
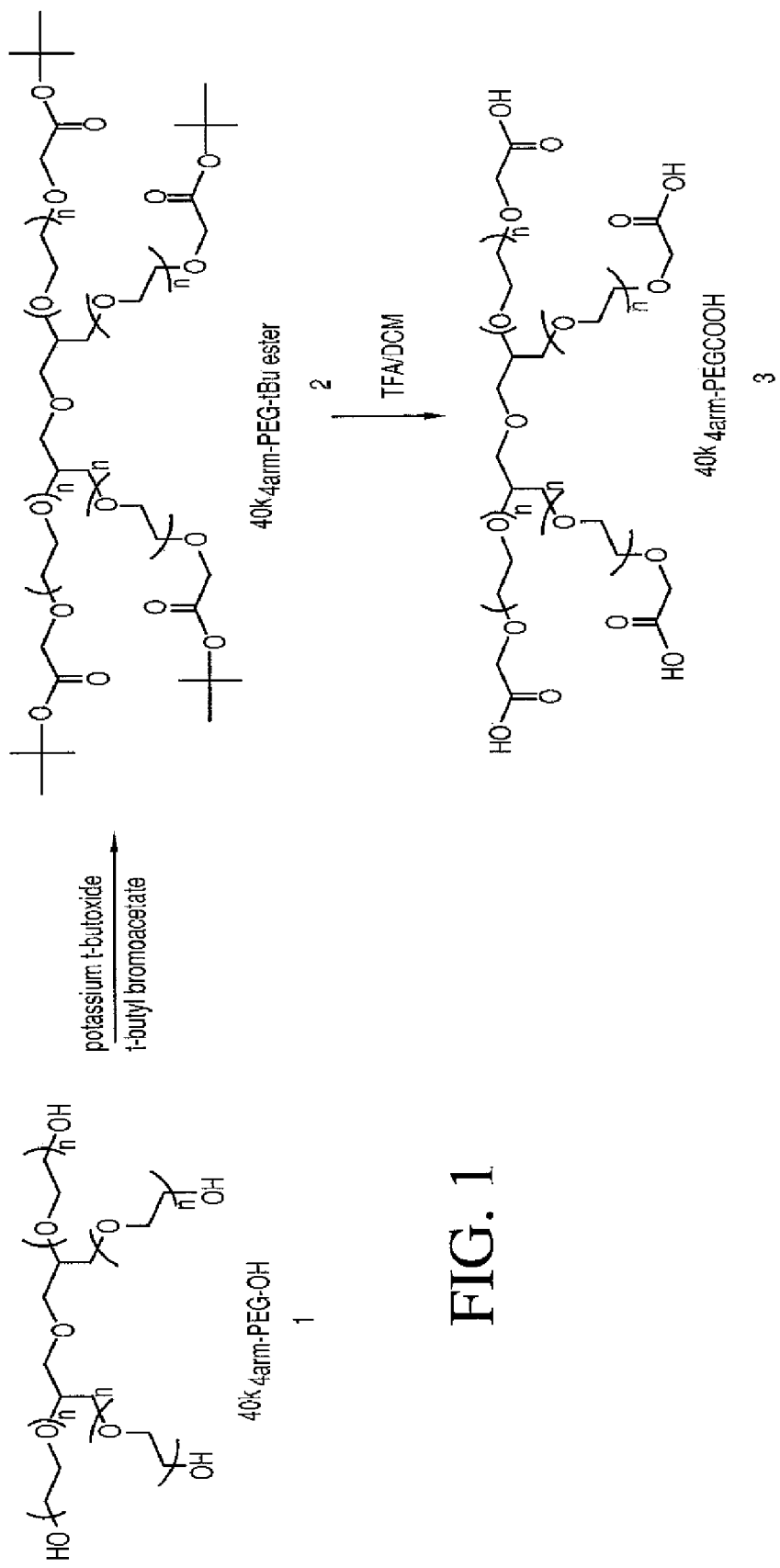
FIG. 1 schematically illustrates a reaction scheme of preparing four-arm polyethylene glycol acids described in Examples 1-2.

The present invention relate to methods of treatment of lymphomas. In one aspect of the present invention, there are provided methods of treating patients having non-Hodgkin's lymphomas. The methods include administering an effective amount of a compound of Formula (I) to patients in need thereof. In one embodiment employed, the compounds of Formula (I) have the structure:

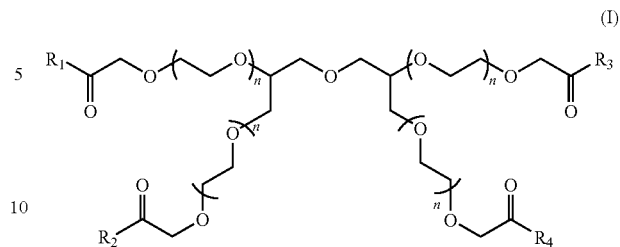

wherein
$R_1$, $R_2$, $R_3$ and $R_4$ are independently OH or $(L)_m$-D;
L is a bifunctional linker;
D is

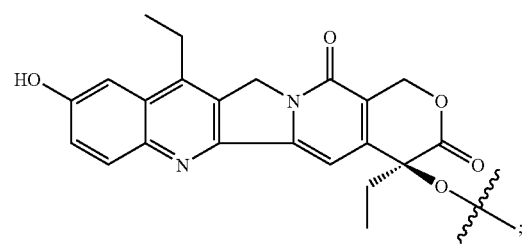

m is 0 or a positive integer preferably from about 1 to about 10, and more preferably 1; and
n is a positive integer, preferably from about 28 to about 341, more preferably from about 114 to about 227, and most preferably about 227;

provided that $R_1$, $R_2$, $R_3$ and $R_4$ are not all OH.

In some preferred aspects, the treatment includes administering a compound having the structure:

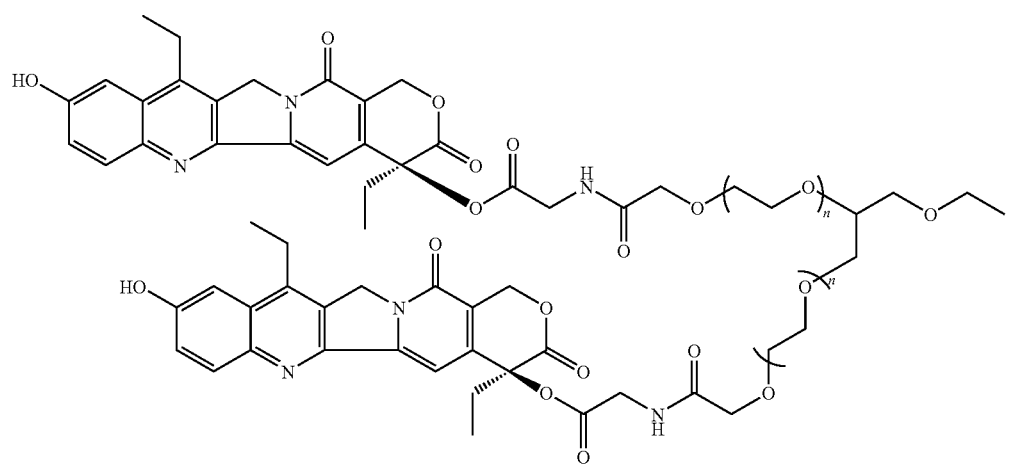

-continued

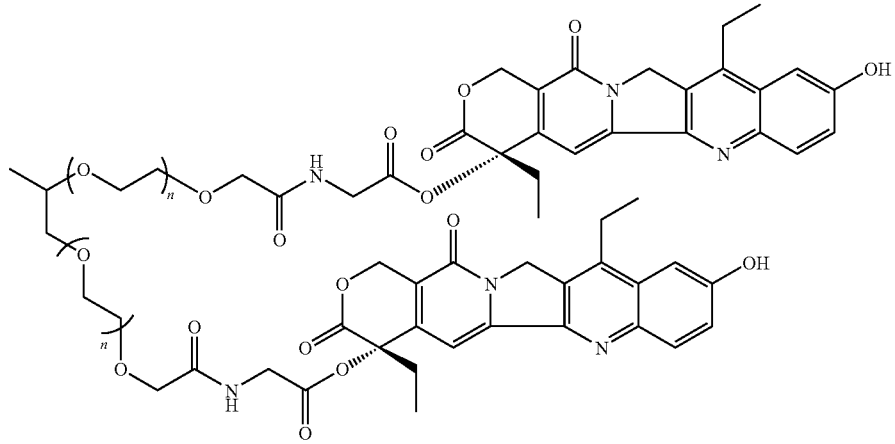

The amount administered can range from about 0.3 mg/m² body surface/dose to about 90 mg/m² body surface/dose. More preferably, the amount administered ranges from about 0.9 mg/m² to about 30 mg/m². For purposes of the present invention, the dosage amount shall be understood to mean the amount of 7-ethyl-10-hydroxycamptothecin not the amount of polymeric conjugate administered.

A. Multi-Art Polymers

The polymer portion of the compounds described herein includes multi-arm PEG's. The multi-arm PEG's are those described in NOF Corp. Drug Delivery System catalog, Ver. 8, April 2006, the disclosure of which is incorporated herein by reference. One particularly preferred multi-arm PEG; has the structure:

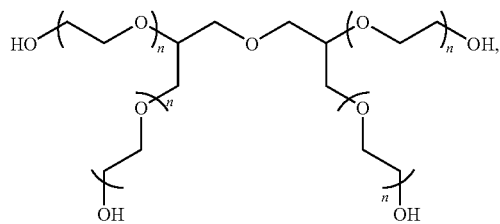

wherein n is a positive integer.

In one preferred embodiment of the invention, the degree of polymerization for the polymer (n) is from about 28 to about 341 to provide polymers having a total molecular weight of from about 5,000 Da to about 60,000 Da, and preferably from about 114 to about 227 to provide polymers having a total molecular weight of from about 20,000 Da to about 40,000 Da. In one particularly preferred embodiment of the invention, n is about 227.

B. Bifunctional Linkers

In certain preferred aspects of the present invention, bifunctional linkers include an amino acid. The amino acid which can be selected from any of the known naturally-occurring L-amino acids is, e.g., alanine, valine, leucine, isoleucine, glycine, serine, threonine, methionine, cysteine, phenylalanine, tyrosine, tryptophan, aspartic acid, glutamic acid, lysine, arginine, histidine, proline, and/or a combination thereof, to name but a few. In alternative aspects, L can be a peptide residue. The peptide can range in size, for instance, from about 2 to about 10 amino acid residues.

Derivatives and analogs of the naturally occurring amino acids, as well as various art-known non-naturally occurring amino acids (D or L), hydrophobic or non-hydrophobic, are also contemplated to be within the scope of the invention. Simply by way of example, amino acid analogs and derivates include:

2-aminoadipic acid, 3-aminoadipic acid, beta-alanine, beta-aminopropionic acid, 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4-aminobutyric acid, desmosine, 2,2-diaminopimelic acid, 2,3-diaminopropionic acid, n-ethylglycine, N-ethylasparagine, 3-hydroxyproline, 4-hydroxyproline, isodesmosine, allo-isoleucine, N-methylglycine or sarcosine, N-methyl-isoleucine, 6-N-methyl-lysine, N-methylvaline, norvaline, norleucine, ornithine, and others too numerous to mention, that are listed in 63 Fed. Reg., 29620, 29622, incorporated by reference herein. Some preferred L groups include glycine, alanine, methionine or sarcosine. More preferably, compounds of the present invention include a glycine as the linker group (L).

In another aspect of the present invention, L after attachment between 7-ethyl-10-hydroxycamptothecin and polymer can be selected among:

—[C(=O)]$_v$(CR$_{22}$R$_{23}$)$_t$—,
—[C(=O)]$_v$(CR$_{22}$R$_{23}$)$_t$—O—,
—[C(=O)]$_v$(CR$_{22}$R$_{23}$)$_t$—NR$_{26}$—,
—[C(=O)]$_v$O(CR$_{22}$R$_{23}$)$_t$—,
—[C(=O)]$_v$O(CR$_{22}$R$_{23}$)$_t$O—,
—[C(=O)]$_v$O(CR$_{22}$R$_{23}$)$_t$NR$_{26}$—,
—[C(=O)]$_v$NR$_{21}$(CR$_{22}$R$_{23}$)$_t$,
—[C(=O)]$_v$NR$_{21}$(CR$_{22}$R$_{23}$)$_t$O—,
—[C(=O)]$_v$NR$_{21}$(CR$_{22}$R$_{23}$)$_t$NR$_{26}$—,
—[C(=O)]$_v$(CR$_{22}$R$_{23}$O)$_t$—,
—[C(=O)]$_v$O(CR$_{22}$R$_{23}$O)$_t$—,
—[C(=O)]$_v$NR$_{21}$(CR$_{22}$R$_{23}$O)$_t$—,
—[C(=O)]$_v$(CR$_{22}$R$_{23}$O)$_t$(CR$_{24}$R$_{25}$)$_y$—,
—[C(=O)]$_v$O(CR$_{22}$R$_{23}$O)$_t$(CR$_{24}$R$_{25}$)$_y$—,
—[C(=O)]$_v$NR$_{21}$(CR$_{22}$R$_{23}$O)$_t$(CR$_{24}$R$_{25}$)$_y$—,
—[C(=O)]$_v$(CR$_{22}$R$_{23}$O)$_t$(CR$_{24}$R$_{25}$)$_y$O—,

—[C(=O)]$_v$(CR$_{22}$R$_{23}$)$_t$(CR$_{24}$R$_{25}$O)$_y$—,
—[C(=O)]$_v$O(CR$_{22}$R$_{23}$O)$_t$(CR$_{24}$R$_{25}$)$_y$O—,
—[C(=O)]$_v$O(CR$_{22}$R$_{23}$)$_t$(CR$_{24}$R$_{25}$O)$_y$—,
—[C(=O)]$_v$NR$_{21}$(CR$_{22}$R$_{23}$O)$_t$(CR$_{24}$R$_{25}$)$_y$O—,
—[C(=O)]$_v$NR$_{21}$(CR$_{22}$R$_{23}$)$_t$(CR$_{24}$R$_{25}$O)$_y$—,
—[C(=O)]$_v$(CR$_{22}$R$_{23}$)$_t$O—(CR$_{28}$R$_{29}$)$_{t'}$—,
—[C(=O)]$_v$(CR$_{22}$R$_{23}$)$_t$NR$_{26}$—(CR$_{28}$R$_{29}$)$_{t'}$—,
—[C(=O)]$_v$(CR$_{22}$R$_{23}$)$_t$S—(CR$_{28}$R$_{29}$)$_{t'}$—,
—[C(=O)]$_v$O(CR$_{22}$R$_{23}$)$_t$O—(CR$_{28}$R$_{29}$)$_{t'}$—,
—[C(=O)]$_v$O(CR$_{22}$R$_{23}$)$_t$NR$_{26}$—(CR$_{28}$R$_{29}$)$_{t'}$—,
—[C(=O)]$_v$O(CR$_{22}$R$_{23}$)$_t$S—(CR$_{28}$R$_{29}$)$_{t'}$—,
—[C(=O)]$_v$NR$_{27}$(CR$_{22}$R$_{23}$)$_t$O—(CR$_{28}$R$_{29}$)$_{t'}$—,
—[C(=O)]$_v$NR$_{21}$(CR$_{22}$R$_{23}$)$_t$NR$_{26}$—(CR$_{28}$R$_{29}$)$_{t'}$—,
—[C(=O)]$_v$NR$_{21}$(CR$_{22}$R$_{23}$)$_t$S—(CR$_{28}$R$_{29}$)$_{t'}$—,
—[C(=O)]$_v$(CR$_{22}$R$_{23}$CR$_{28}$R$_{29}$O)$_t$NR$_{26}$—,
—[C(=O)]$_v$(CR$_{22}$R$_{23}$CR$_{28}$R$_{29}$O)$_t$—,
—[C(=O)]$_v$O(CR$_{22}$R$_{23}$CR$_{28}$R$_{29}$O)$_t$NR$_{26}$—,
—[C(=O)]$_v$O(CR$_{22}$R$_{23}$CR$_{28}$R$_{29}$O)$_t$—,
—[C(=O)]$_v$NR$_{21}$(CR$_{22}$R$_{23}$CR$_{28}$R$_{29}$O)$_t$NR$_{26}$—,
—[C(=O)]$_v$NR$_{21}$(CR$_{22}$R$_{23}$CR$_{28}$R$_{29}$O)$_t$—,
—[C(=O)]$_v$(CR$_{22}$R$_{23}$CR$_{28}$R$_{29}$O)$_t$(CR$_{24}$R$_{25}$)$_y$—,
—[C(=O)]$_v$O(CR$_{22}$R$_{23}$CR$_{28}$R$_{29}$O)$_t$(CR$_{24}$R$_{25}$)$_y$—,
—[C(=O)]$_v$NR$_{21}$(CR$_{22}$R$_{23}$CR$_{28}$R$_{29}$O)$_t$(CR$_{24}$R$_{25}$)$_y$—,
—[C(=O)]$_v$(CR$_{22}$R$_{23}$CR$_{28}$R$_{29}$O)$_t$(CR$_{24}$R$_{25}$)$_y$O—,
—[C(=O)]$_v$(CR$_{22}$R$_{23}$)$_t$(CR$_{24}$R$_{25}$CR$_{28}$R$_{29}$O)$_y$—,
—[C(=O)]$_v$(CR$_{22}$R$_{23}$)$_t$(CR$_{24}$R$_{25}$CR$_{28}$R$_{29}$O)$_y$NR$_{26}$—,
—[C(=O)]$_v$O(CR$_{22}$R$_{23}$CR$_{28}$R$_{29}$O)$_t$(CR$_{24}$R$_{25}$)$_y$O—,
—[C(=O)]$_v$O(CR$_{22}$R$_{23}$)$_t$(CR$_{24}$R$_{25}$CR$_{28}$R$_{29}$O)$_y$—,
—[C(=O)]$_v$O(CR$_{22}$R$_{23}$)$_t$(CR$_{24}$CR$_{25}$CR$_{28}$R$_{29}$O)$_y$NR$_{26}$—,
—[C(=O)]$_v$NR$_{21}$(CR$_{22}$R$_{23}$CR$_{28}$R$_{29}$O)$_t$(CR$_{24}$R$_{25}$)$_y$O—,
—[C(=O)]$_v$NR$_{21}$(CR$_{22}$R$_{23}$)$_t$(CR$_{24}$R$_{25}$CR$_{28}$R$_{29}$O)$_y$—,
—[C(=O)]$_v$NR$_{21}$(CR$_{22}$R$_{23}$)$_t$(CR$_{24}$R$_{25}$CR$_{28}$R$_{29}$O)$_y$NR$_{26}$—,

—[C(=O)]$_v$O(CR$_{22}$R$_{23}$)$_y$—⟨C$_6$H$_4$(R$_{27}$)⟩—(CR$_{24}$R$_{25}$)$_t$NR$_{26}$—,

—[C(=O)]$_v$O(CR$_{22}$R$_{23}$)$_y$—⟨C$_6$H$_4$(R$_{27}$)⟩—(CR$_{24}$R$_{25}$)$_t$O—,

—[C(=O)]$_v$NR$_{21}$(CR$_{22}$R$_{23}$)$_y$—⟨C$_6$H$_4$(R$_{27}$)⟩—(CR$_{24}$R$_{25}$)$_t$NR$_{26}$—, and —[C(=O)]$_v$NR$_{21}$(CR$_{22}$R$_{23}$)$_y$—⟨C$_6$H$_4$(R$_{27}$)⟩—(CR$_{24}$R$_{25}$)$_t$O— wherein:

R$_{21}$-R$_{29}$ are independently selected from the group consisting of hydrogen, amino, substituted amino, azido, carboxy, cyano, halo, hydroxyl, nitro, silyl ether, sulfonyl, mercapto, C$_{1-6}$ alkylmercapto, arylmercapto, substituted arylmercapto, substituted C$_{1-6}$ alkylthio, C$_{1-6}$ alkyls, C$_{2-6}$ alkenyl, C$_{2-6}$ alkynyl, C$_{3-19}$ branched alkyl, C$_{3-8}$ cycloalkyl, C$_{1-6}$ substituted alkyl, C$_{2-6}$ substituted alkenyl, C$_{2-6}$ substituted alkynyl, C$_{3-8}$ substituted cycloalkyl, aryl, substituted aryl, heteroaryl, substituted heteroaryl, C$_{1-6}$ heteroalkyl, substituted C$_{1-6}$ heteroalkyl, C$_{1-6}$ alkoxy, aryloxy, C$_{1-6}$heteroalkoxy, heteroaryloxy, C$_{2-6}$ alkanoyl, arylcarbonyl, C$_{2-6}$ alkoxycarbonyl, aryloxycarbonyl, C$_{2-6}$ alkanoyloxy, arylcarbonyloxy, C$_{2-6}$ substituted alkanoyl, substituted arylcarbonyl, C$_{2-6}$ substituted alkanoyloxy, substituted aryloxycarbonyl, C$_{2-6}$ substituted alkanoyloxy, substituted and arylcarbonyloxy;

(t), (t') and (y) are independently selected from zero or a positive integer, preferably from about 1 to about 10; and (v) is 0 or 1.

In some preferred embodiments, L can include:
—[C(=O)]$_v$(CH$_2$)$_t$—,
—[C(=O)]$_v$(CH$_2$)$_t$—O—,
—[C(=O)]$_v$(CH$_2$)$_t$—NR$_{26}$—,
—[C(=O)]$_v$O(CH$_2$)$_t$—,
—[C(=O)]$_v$O(CH$_2$)$_t$O—,
—[C(=O)]$_v$O(CH$_2$)$_t$NH—,
—[C(=O)]$_v$NH(CH$_2$)$_t$—,
—[C(=O)]$_v$NH(CH$_2$)$_t$O—,
—[C(=O)]$_v$NH(CH$_2$)$_t$NH—,
—[C(=O)]$_v$(CH$_2$O)$_t$—,
—[C(=O)]$_v$O(CH$_2$O)$_t$—,
—[C(=O)]$_v$NH(CH$_2$O)$_t$—,
—[C(=O)]$_v$(CH$_2$O)$_t$(CH$_2$)$_y$—,
—[C(=O)]$_v$O(CH$_2$O)$_t$H$_2$)$_y$—,
—[C(=O)]$_v$NH(CH$_2$O)$_t$(CH$_{25}$)$_y$—,
—[C(=O)]$_v$(CH$_2$O)$_t$(CH$_2$)$_y$O—,
—[C(=O)]$_v$(CH$_2$)$_t$(CH$_2$O)$_y$—,
—[C(=O)]$_v$O(CH$_2$O)$_t$(CH$_2$)$_y$O—,
—[C(=O)]$_v$O(CH$_2$)$_t$(CH$_2$O)$_y$—,
—[C(=O)]$_v$NH(CH$_2$O)$_t$(CH$_2$)$_y$O—,
—[C(=O)]$_v$NH(CR$_{22}$R$_{23}$)$_t$(CH$_2$O)$_y$—,
—[C(=O)]$_v$(CH$_2$)$_t$O—(CH$_2$)$_{t'}$—,
—[C(=O)]$_v$(CH$_2$)$_t$NH—(CH$_2$)$_{t'}$—,
—[C(=O)]$_v$(CH$_2$)$_t$S—(CH$_2$)$_{t'}$—,
—[C(=O)]$_v$O(CH$_2$)$_t$O—(CH$_2$)$_{t'}$—,
—[C(=O)]$_v$O(CH$_2$)$_t$NH—(CH$_2$)$_{t'}$—,
—[C(=O)]$_v$O(CH$_2$)$_t$S—(CH$_2$)$_{t'}$—,
—[C(=O)]$_v$NH(CR$_{22}$R$_{23}$)$_t$O—(CH$_2$)$_{t'}$—,
—[C(=O)]$_v$NH(CH$_2$)$_t$NH—(CH$_2$)$_{t'}$—,
—[C(=O)]$_v$NH(CH$_2$)$_t$S—(CH$_2$)$_{t'}$—,
—[C(=O)]$_v$(CH$_2$CH$_2$O)$_t$NR$_{26}$—,
—[C(=O)]$_v$(CH$_2$CH$_2$O)$_t$—,
—[C(=O)]$_v$O(CH$_2$CH$_2$O)$_t$NH—,
—[C(=O)]$_v$O(CH$_2$CH$_2$O)$_t$—,
—[C(=O)]NH(CH$_2$CH$_2$O)$_t$NH—,
—[C(=O)]$_v$NH(CH$_2$CH$_2$O)$_t$—,
—[C(=O)]$_v$(CH$_2$CH$_2$O)$_t$(CH$_2$)$_y$—,
—[C(=O)]$_v$O(CH$_2$CH$_2$O)$_t$(CH$_2$)$_y$—,
—[C(=O)]$_v$NH(CH$_2$CH$_2$O)$_t$(CH$_2$)$_y$—,
—[C(=O)]$_v$(CH$_2$CH$_2$O)$_t$(CH$_2$)$_y$O—,
—[C(=O)]$_v$(CH$_2$)$_t$(CH$_2$CH$_2$O)$_y$—,
—[C(=O)]$_v$(CH$_2$)$_t$(CH$_2$CH$_2$O)$_y$NH—,
—[C(=O)]$_v$O(CH$_2$CH$_2$O)$_t$(CH$_2$)$_y$O—,
—[C(=O)]$_v$O(CH$_2$)$_t$(CH$_2$CH$_2$O)$_y$—,
—[C(=O)]$_v$O(CH$_2$)$_t$(CH$_2$CH$_2$O)$_y$NH—,
—[C(=O)]$_v$NH(CH$_2$CH$_2$O)$_t$(CH$_2$)$_y$O—,
—[C(=O)]$_v$NH(CH$_2$)$_t$(CH$_2$CH$_2$O)$_y$—,
—[C(=O)]$_v$NH(CH$_2$)$_t$(CH$_2$CH$_2$O)$_y$NH—, —[C(=O)]$_v$O(CH$_2$)$_y$—⟨C$_6$H$_4$⟩—(CH$_2$)$_t$O,

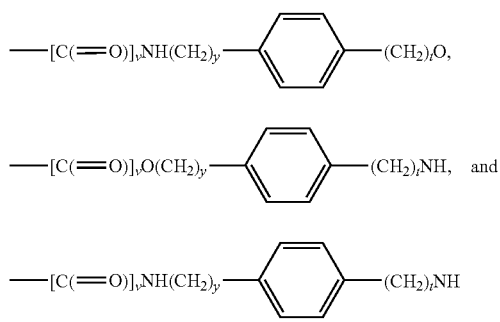

wherein (t), (t') and (y) are independently selected from zero or a positive integer, preferably from about 1 to about 10; and (v) is 0 or 1.

In another preferred aspect of the present invention, the compounds include one up to 10 units of the bifunctional Tinker. More preferably, one unit of the bifunctional linker is included and thus m is 1.

Additional linkers are found in Table 1 of Greenwald et al. (*Bioorganic & Medicinal Chemistry*, 1998, 6:551-562), the contents of which are incorporated by reference herein.

C. Synthesis of Prodrugs

Generally, the prodrugs of the invention employed in treatment are prepared by reacting one or more equivalents of an activated multi-arm polymer with, for example, one or more equivalents per active site of 7-ethyl-10-hydroxycamptothecin-amino acid conjugate under conditions which are sufficient to effectively cause the amino group to undergo a reaction with the carboxylic acid of the polymer and form a linkage.

More specifically, the methods can include:

1) providing one equivalent of 7-ethyl-10-hydroxycamptothecin containing an available 20-hydroxyl group and one or more equivalents of a bifunctional linker containing an available carboxylic acid group;

2) reacting the two reactants to form a 7-ethyl-10-hydroxy-camptothecin-bifunctional linker intermediate in an inert solvent such as DCM (or DMF, chloroform, toluene or mixtures thereof) in the presence of a coupling reagent such as 1,(3-dimethyl aminopropyl) 3-ethyl carbodiimide (EDC), (or 1,3-diisopropylcarbodiimide (DIPC), any suitable dialkyl carbodiimide, Mukaiyama reagents, (e.g. 2-halo-1-alkyl-pyridinium halides) or propane phosphonic acid cyclic anhydride (PPACA), etc) and a suitable base such as DMAP; and 3) reacting one or more equivalents per active site (fore example, 2 equivalents were used in Example 6) of the resulting intermediate having an amine group and one equivalent of an activated polymer, such as a PEG-acid in an inert solvent such as DCM (or DMF, chloroform, toluene or mixtures thereof) in the presence of a coupling reagent such as 1,(3-dimethyl aminopropyl) 3-ethyl carbodiimide (EDC), PPAC (or 1,3-diisopropylcarbodiimide (DIPC), any suitable dialkyl carbodiimide, Mukaiyama reagents, (e.g. 2-halo-1-alkyl-pyridinium halides) or propane phosphonic acid cyclic anhydride PPACA), etc.), and a suitable base such as DMAP, which are available, for example, from commercial sources such as Sigma Chemical, or synthesized using known techniques, at a temperature from 0° C. up to 22° C.

In one preferred aspect, the 10-hydroxyl group of 7-ethyl-10-hydroxycamptothecin is protected prior to step 1).

Aromatic protecting groups for the 10-hydroxyl group in 7-ethyl-10-hydroxy-camptothecin are preferred because 7-ethyl-10-hydroxycamptothecin intermediates thereof have better solubility and can be purified in highly pure form efficiently and effectively. For example, silyl-containing protecting groups such as TBDPSCT, TBDMSCl and TMSCT can be used to protect the 10-hydroxyl group in 7-ethyl-10-hydroxycamptothecin.

The activated polymer, i.e., a polymer containing 1-4 terminal carboxyl acid groups can be prepared, for example, by converting NOF Sunbright-type or other branched polymers having terminal OH groups into the corresponding carboxyl acid derivatives using standard techniques well known to those of ordinary skill. See, for example, Examples 1-2 herein as well as commonly assigned U.S. Pat. No. 5,605,976, the contents of which are incorporated herein by reference.

The first and second coupling agents can be the same or different.

Examples of preferred bifunctional linker groups include glycine, alanine, methionine, sarcosine, etc. Alternative syntheses can be used without undue experimentation.

According to the present invention, the compounds administered include:

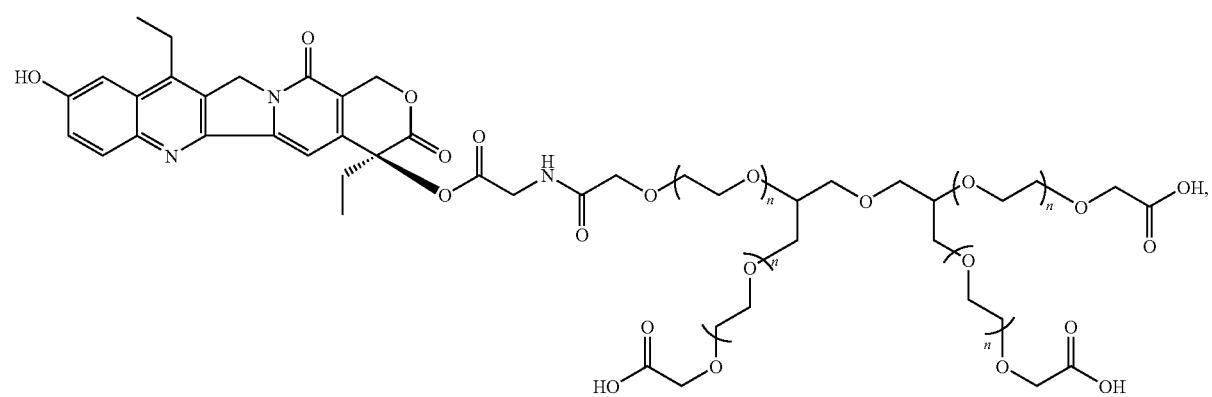

-continued
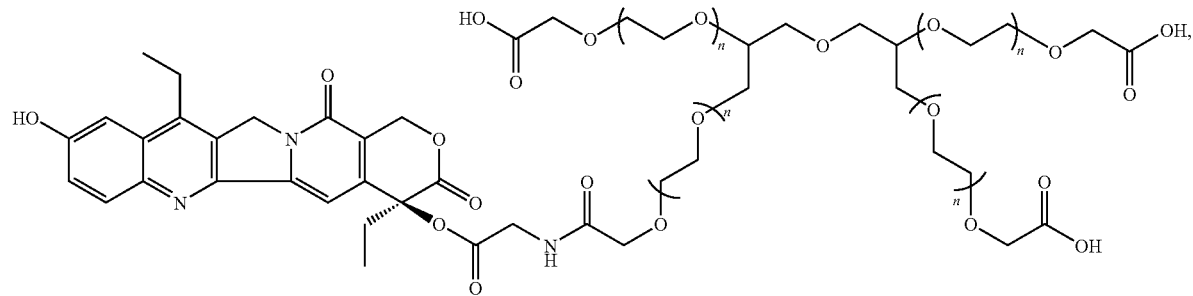
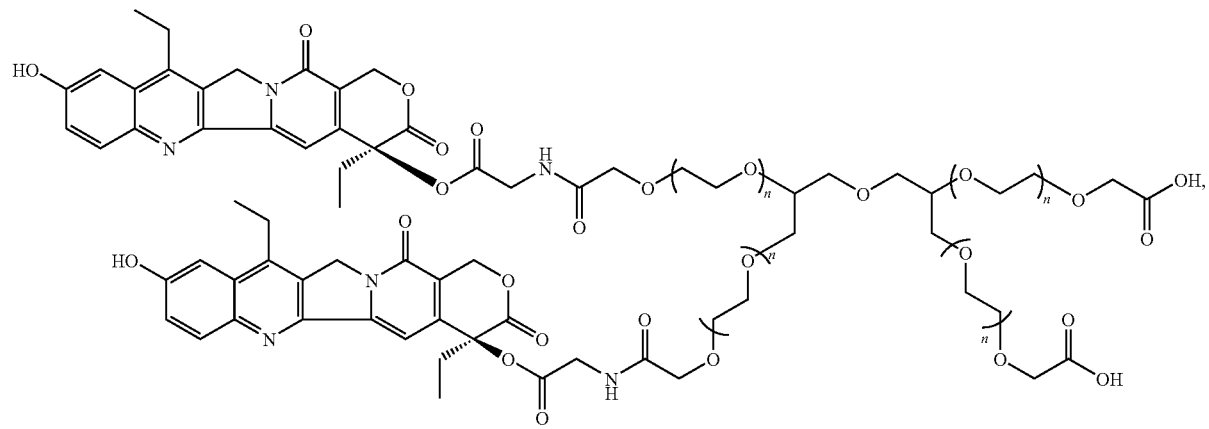
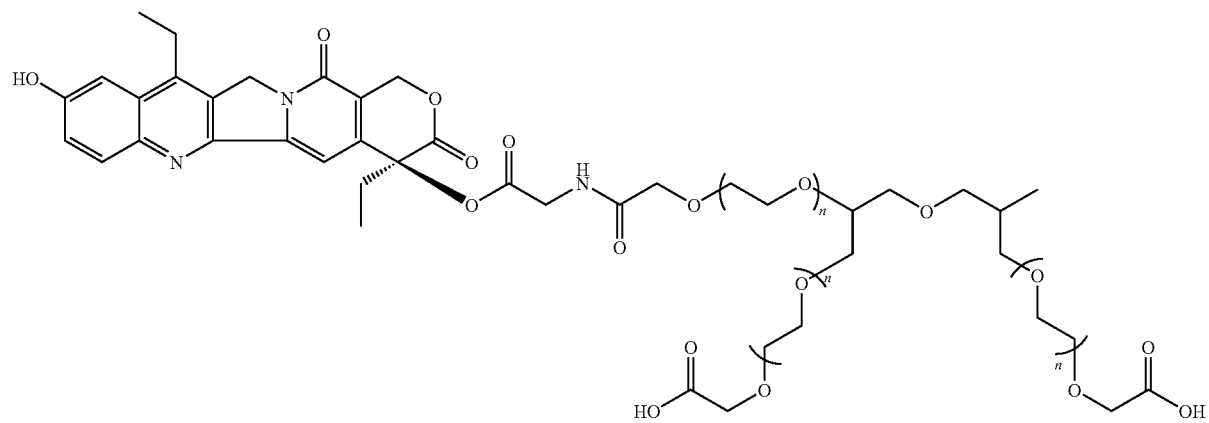
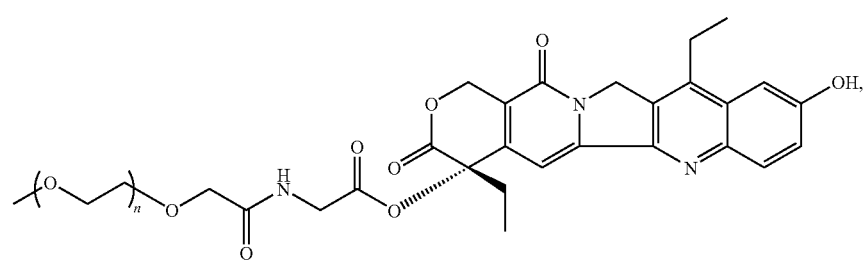

-continued
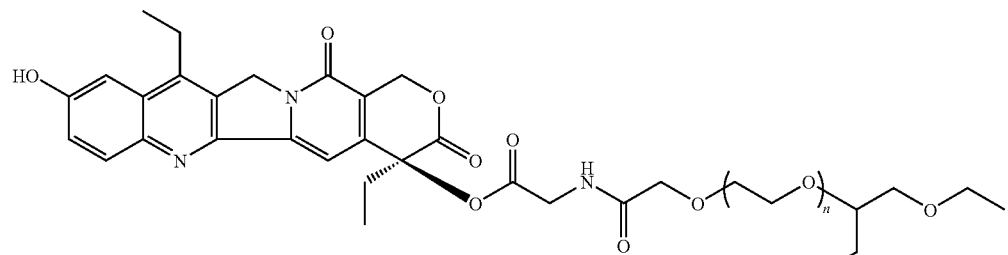
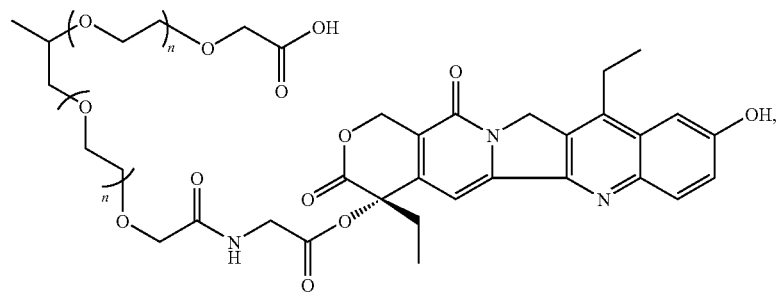
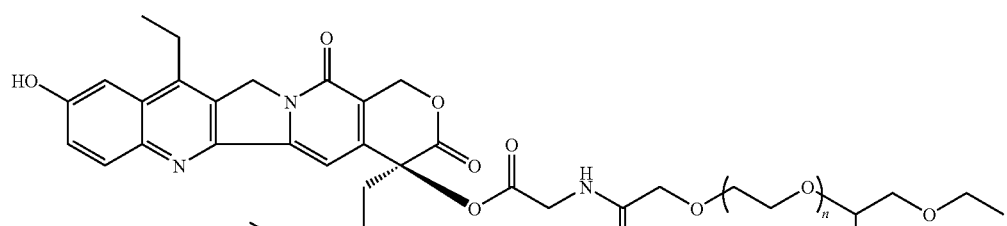
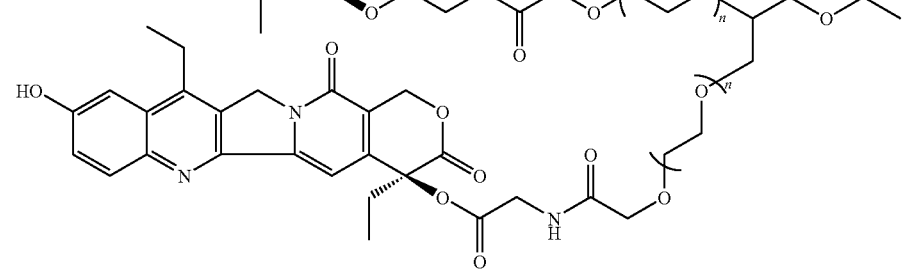
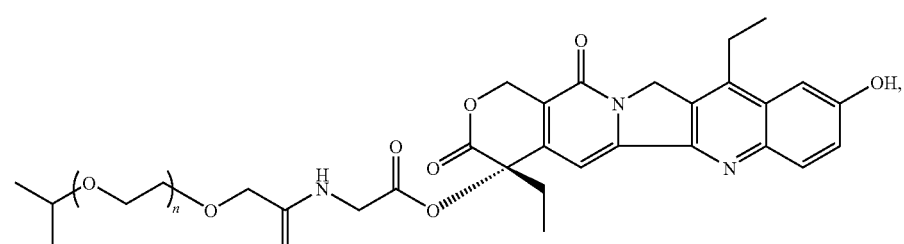

-continued
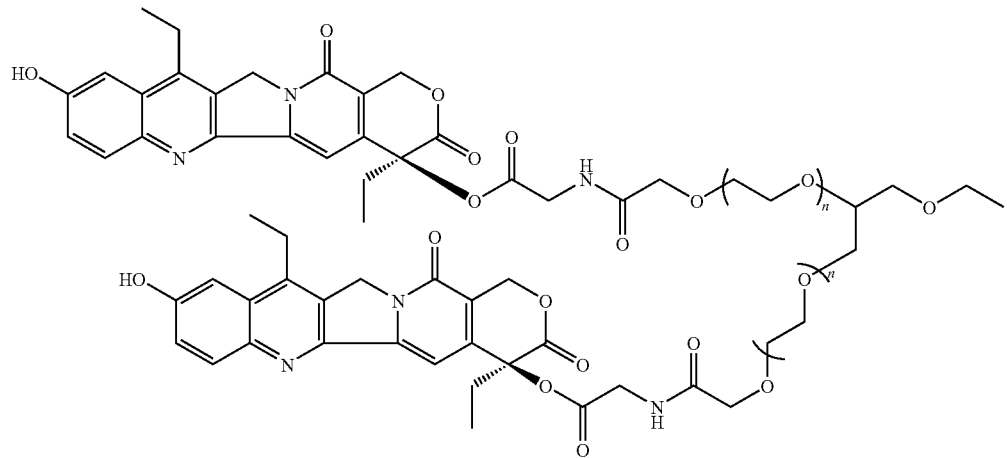
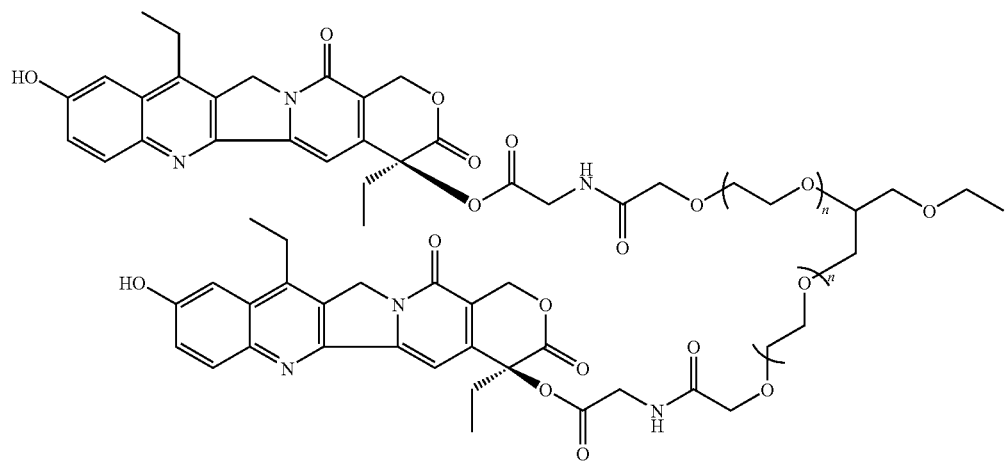
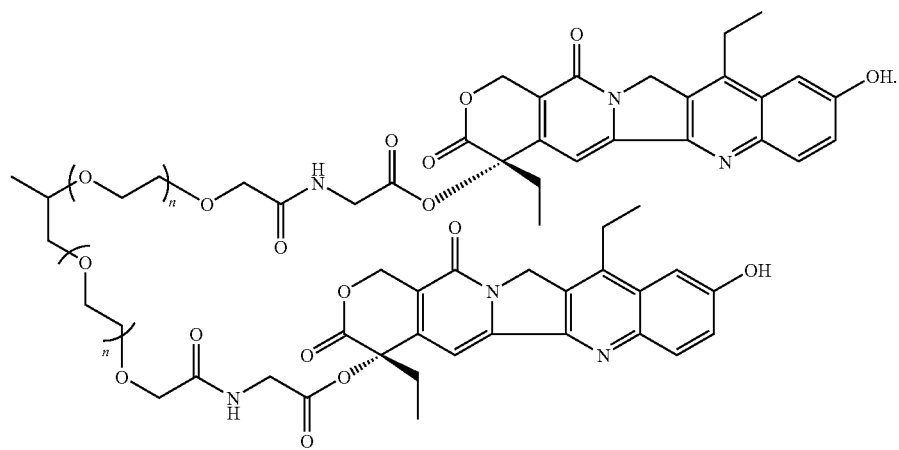

One particularly preferred treatment includes administering a compound having the structure

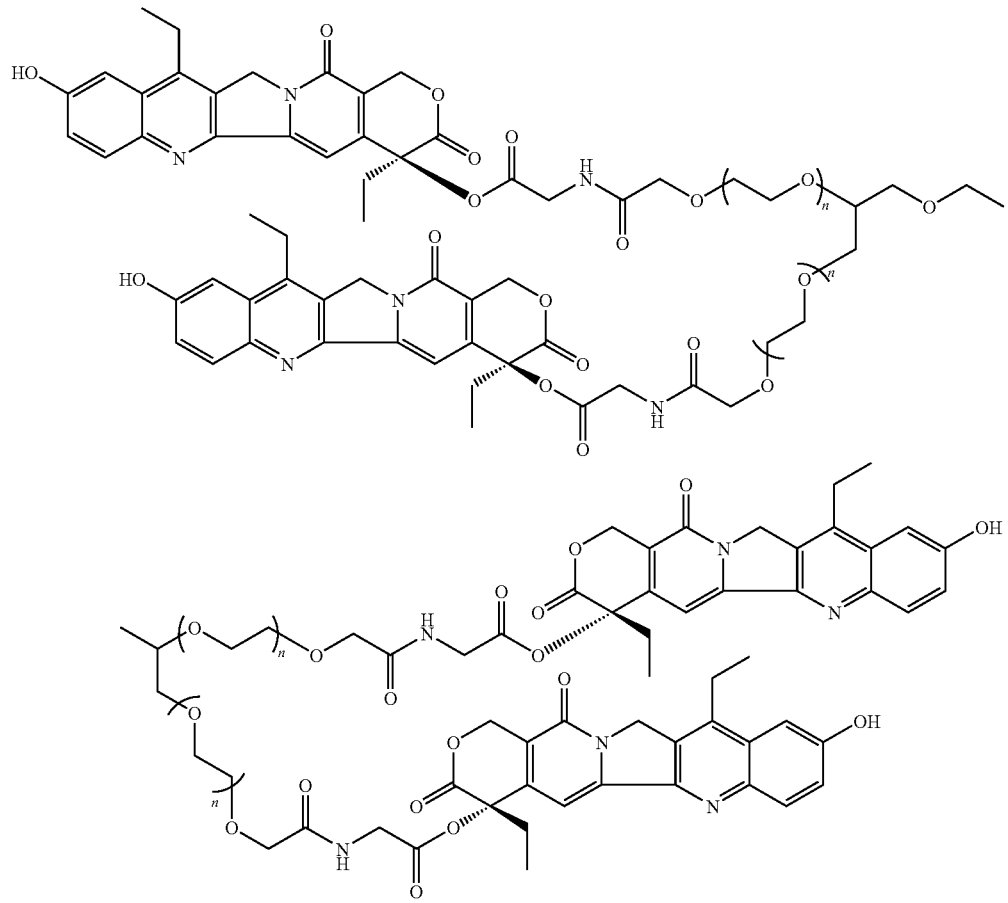

wherein all four arms of the polymer are conjugated to 7-ethyl-10-hydroxycamptothecin through glycine and the polymer portion has molecular weight of about 40,000 daltons D. Compositions/Formulations Pharmaceutical compositions containing the polymer conjugates of the present invention may be manufactured by processes well known in the art, e.g., using a variety of well-known mixing, dissolving, granulating, levigating, emulsifying, encapsulating, entrapping or lyophilizing processes. The compositions may be formulated in conjunction with one or more physiologically acceptable carriers comprising excipients and auxiliaries which facilitate processing of the active compounds into preparations which can be used pharmaceutically. Proper formulation is dependent upon the route of administration chosen. Parenteral routes are preferred in many aspects of the invention.

For injection, including, without limitation, intravenous, intramuscular and subcutaneous injection, the compounds of the invention may be formulated in aqueous solutions, preferably in physiologically compatible buffers such as physiological saline buffer or polar solvents including, without limitation, a pyrrolidone or dimethylsulfoxide.

The compounds described herein may also be formulated for parenteral administration, e.g., by bolus injection or continuous infusion. Formulations for injection may be presented in unit dosage form, e.g., in ampoules or in multi-dose containers. Useful compositions include, without limitation, suspensions, solutions or emulsions in oily or aqueous vehicles, and may contain adjuncts such as suspending, stabilizing and/or dispersing agents. Pharmaceutical compositions for parenteral administration include aqueous solutions of a water soluble form, such as, without limitation, a salt (preferred) of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances that increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions. Alternatively, the active ingredient may be in powder form for constitution with a suitable vehicle, e.g., sterile, pyrogen-free water, before use.

For oral administration, the compounds can be formulated by combining the active compounds with pharmaceutically acceptable carriers well-known in the art. Such carriers enable the compounds of the invention to be formulated as tablets, pills, lozenges, dragees, capsules, liquids, gels, syrups, pastes, slurries, solutions, suspensions, concentrated solutions and suspensions for diluting in the drinking water of a patient, premixes for dilution in the feed of a patient, and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropyl- methylcellulose, sodium carboxy-methylcellulose, and/or polyvinylpyrrolidone (PVP). If desired, disintegrating agents may be added, such as cross-linked polyvinyl pyrrolidone, agar, or alginic acid. A salt such as sodium alginate may also be used.

For administration by inhalation, the compounds of the present invention can conveniently be delivered in the form of an aerosol spray using a pressurized pack or a nebulizer and a suitable propellant.

The compounds may also be formulated in rectal compositions such as suppositories or retention enemas, using, e.g., conventional suppository bases such as cocoa butter or other glycerides.

In addition to the formulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

Other delivery systems such as liposomes and emulsions can also be used.

Additionally, the compounds may be delivered using a sustained-release system, such as semi-permeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the particular compound, additional stabilization strategies may be employed.

E. Dosages

A therapeutically effective amount refers to an amount of a compound effective to prevent, alleviate or ameliorate 7-ethyl-10-hydroxycamptothecin-susceptible condition. Determination of a therapeutically effective amount is well within the capability of those skilled in the art, especially in light of the disclosure herein.

For any compound used in the methods of the present invention, the therapeutically effective amount can be estimated initially from in vitro assays. Then, the dosage can be formulated for use in animal models so as to achieve a circulating concentration range that includes the effective dosage. Such information can then be used to more accurately determine dosages useful in patients.

Toxicity and therapeutic efficacy of the compounds described herein can be determined by standard pharmaceutical procedures in cell cultures or experimental animals using methods well-known in the art. The dosage, of course, can vary depending upon the dosage form and route of administration. The exact formulation, route of administration and dosage can be selected by the individual physician in view of the patient's condition.

In general, however, the presently preferred dosage range for systemic delivery of a compound of this invention will be from about 1 to about 100 mg/kg/week and is preferably from about 2 to about 60 mg/kg/week.

In one preferred aspect, the treatment of the present invention includes administering the compounds described herein in an amount of from about 0.3 mg/m$^2$ body surface/dose to about 90 mg/m$^2$ body surface/dose. More preferably, the amounts of the compounds described herein range from about 0.9 mg/m$^2$ body surface/dose to about 30 mg/m$^2$ body surface/dose.

The treatment protocol can be based on a single dose administered once daily or divided into multiple doses which can be given as part of a multi-week treatment protocol. The precise dose will depend on the stage and severity of the condition, the susceptibility of the tumor to the polymer-prodrug composition, and the individual characteristics of the patient being treated, as will be appreciated by one of ordinary skill in the art.

It is also contemplated that the treatment will be given for one or more days until the desired clinical result is obtained.

In some preferred aspects, the treatment protocol includes administering the amount ranging from about 1 mg/m$^2$ body surface/dose to about 16 mg/m$^2$ body surface/dose weekly for three weeks, followed by 1 week without treatment and repeating for about 3 cycles. The amount administered per every three weeks can range from about 1.25 mg/m$^2$ body surface/dose to about 45 mg/m$^2$ body surface/dose.

Alternatively, the compounds administered can be based on body weight. Thus, the amounts can range from about 0.1 mg/kg body weight/dose to about 30 mg/kg body weight/dose, preferably, from about 0.3 mg/kg to about 10 mg/kg. Specific doses such as 10 mg/kg at q2d×5 regimen (multiple dose) or 30 mg/kg on a single dose regimen can be administered.

In all aspects of the invention where polymeric conjugates are administered, the dosage amount mentioned is based on the amount of 7-ethyl-10-hydroxycamptothecin rather than the amount of polymeric conjugate administered.

Further aspects of the present invention include combining the compounds described herein with other anticancer therapies for synergistic or additive benefit.

F. Treatment of Non-Hodgkiin's Lymphomas

The present invention provides methods of treatment of lymphomas. In one preferred aspect, the present invention provides methods of treating patients with non-Hodgkin's lymphomas. For purposes of the present invention, "treatment" or "cure" shall be understood to mean inhibition, reduction, amelioration and prevention of tumor growth, tumor burden and metastasis, remission of tumor, or prevention of recurrences of tumor and/or neoplastic growths in patients after completion of treatment.

The non-Hodgkin's lymphomas being treated can include aggressive (fast-growing) and indolent (slow-growing) types. Alternatively, the non-Hodgkin's lymphomas can include B-cell or T-cell NHL. A non-limiting list of the B-cell NHL includes Burkitt's lymphoma, diffuse large B-cell lymphoma, follicular lymphoma, immunoblastic large cell lymphoma, precursor B-lymphoblastic lymphoma, mantle cell lymphoma, chronic lymphocytic leukima (CLL)/small lymphocytic lymphoma (SLL), extranodal marginal zone B-cell lymphoma-mucosa-associated lymphoid tissue (MALT) lymphoma, nodal marginal zone B-cell lymphoma, splenic marginal zone B-cell lymphoma, primary mediastinal B-cell lymphoma, lymphoplasmocytic lymphoma, hairy cell leukimia, and primary central nervous system (CNS) lymphoma. The T-cell NHL includes mycosis fungoides, anaplastic large cell lymphoma, angioimmunoblastic T-cell lymphoma, extranodal natural killer/T-cell lymphoma, enteropathy type T-cell lymphoma, subcutaneous panniculitis-like T-cell lymphoma, precursor T-lymphoblastic lymphoma. Additional non-Hodgkin's lymphomas are contemplated within the scope of the present invention and apparent to those of ordinary skill in the art.

In alternative aspects, the treatment involves lymphomas related to lymphoproliferative disorders following bone marrow or stem cell transplantation such as B-cell NHL.

EXAMPLES

Figure 2:
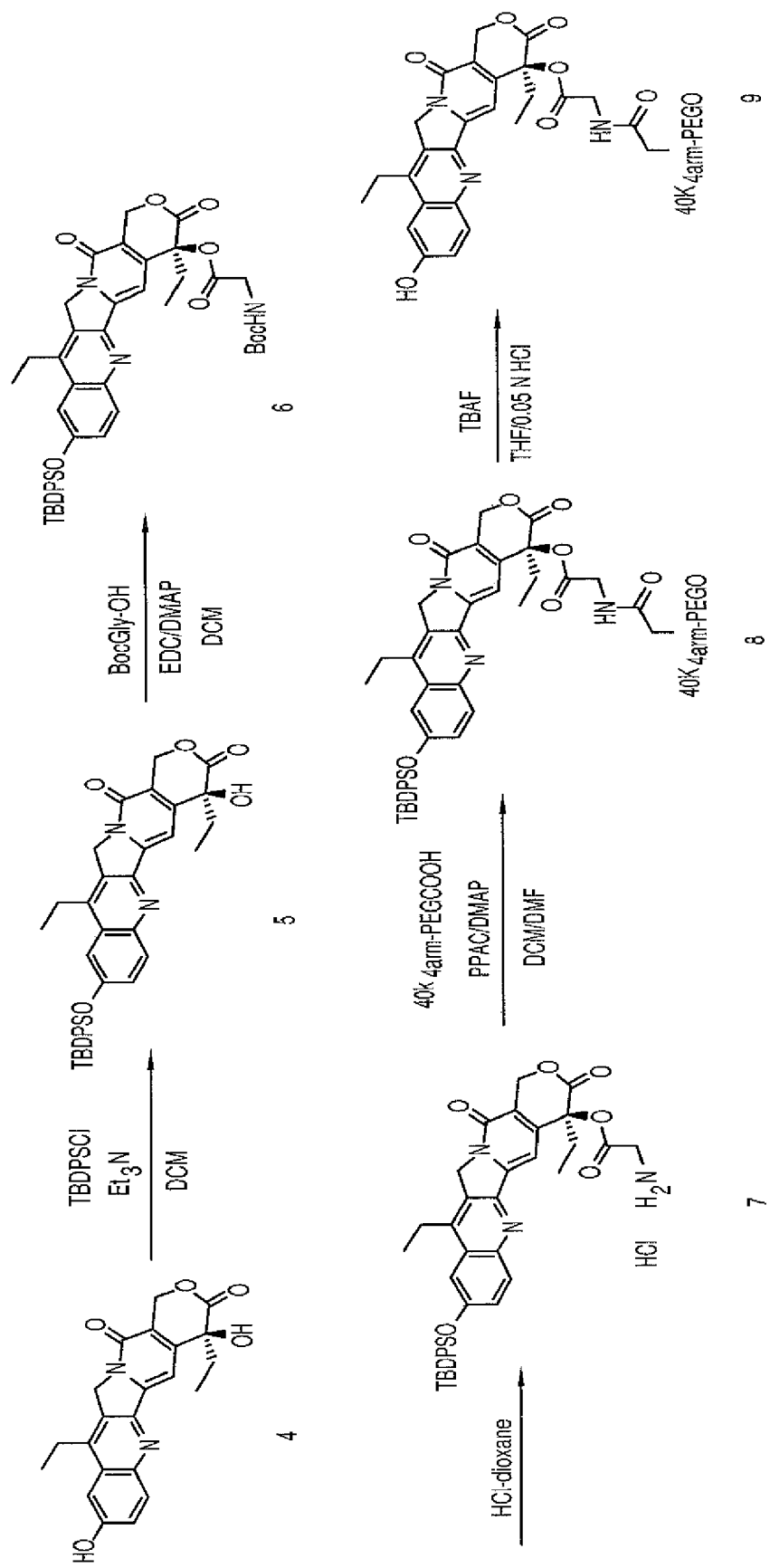
FIG. 2 schematically illustrates a reaction scheme of preparing 4arm-PEG-Gly-(7-ethyl-10-hydroxycamptothecin) described in Examples 3-7.

The following examples serve to provide further appreciation of the invention but are not meant in any way to restrict the effective scope of the invention. The underlined and bold-faced numbers recited in the Examples correspond to those shown in the FIGS. 1-2.

General Procedures. All reactions were run under an atmosphere of dry nitrogen or argon. Commercial reagents were used without further purification. All PEG compounds were dried under vacuum or by azeotropic distillation from toluene prior to use. $^{13}$C NMR spectra were obtained at 75.46 MHz using a Varian Mercury®300 NMR spectrometer and deuterated chloroform and methanol as the solvents unless otherwise specified. Chemical shifts (δ) are reported in parts per million (ppm) downfield from tetramethylsilane (TMS). HPLC Method. The reaction mixtures and the purity of intermediates and final products were monitored by a Beckman Coulter System Gold® HPLC instrument. It employs a ZOBAX® 300SB C8 reversed phase column (150×4.6 mm) or a Phenomenex Jupiter® 300A C18 reversed phase column (150×4.6 mm) with a multiwavelength UV detector, using a gradient of 10-90% of acetonitrile in 0.05% trifluoroacetic acid (TFA) at a flow rate of 1 mL/min.)

Example 1

$^{40k}$4arm-PEG-tBu Ester (Compound 2)

$^{40k}$4arm-PEG-OH (12.5 g, 1 eq.) was azeotroped with 220 mL of toluene to remove 35 mL of toluene/water. The solution was cooled to 30° C. and 1.0 M potassium t-butoxide in t-butanol (3.75 mL, 3eq×4=12 eq.) was added. The mixture was stirred at 30° C. for 30 min and then t-butyl bromoacetate (0.975 g, 4 eq.×4=16 eq.) was added. The reaction was kept at 30° C. for 1 hour and then was cooled to 25° C. 150 mL of ether was slowly added to precipitate product. The resulting suspension was cooled to 17° C. and stayed at 17° C. for half hour. The crude product was filtered and the wet cake was washed with ether twice (2×125 mL). The isolated wet cake was dissolved in 50 ml of DCM and the product was precipitated with 350 ml of ether and filtered. The wet cake was washed with ether twice (2×125 mL). The product was dried under vacuum at 40° C. (yield=98%, 12.25 g). $^3$C NMR (75.4 MHz, CDCl$_3$): δ 27.71, 68.48-70.71 (PEG), 80.94, 168.97.

Example 2

$^{40k}$4arm-PEG Acid (Compound 3)

$^{40k}$4arm-PEG-tBu ester (compound 2, 12 g) was dissolved in 120 mL of DCM and then 60 mL of TFA were added. The mixture was stirred at room temperature for 3 hours and then the solvent was removed under vacuum at 35° C. The resulting oil residue was dissolved in 37.5 mL of DCM. The crude product was precipitated with 375 mL of ether. The wet cake was dissolved in 30 mL of 0.5% NaHCO$_3$. The product was extracted with DCM twice (2×150 ml). The combined organic layers were dried over 2.5 g of MgSO$_4$. The solvent was removed under vacuum at room temperature. The resulting residue was dissolved in 37.5 mL of DCM and the product was precipitated with 300 mL of ether and filtered. The wet cake was washed with ether twice (2×125ml). The product was dried under vacuum at 40° C. (yield=90%, 10.75 g). $^{13}$C NMR (75.4 MHz, CDCl$_3$): 6 67.93-71.6 CPEG), 170.83.

Example 3

TBDPS-(10)-(7-ethyl-10-hydroxycamptothecin) (Compound 5)

To a suspension of 7-ethyl-10-hydroxycamptothecin (compound 4, 2.0 g, 5.10 mmol, 1 eq.) in 100 mL of anhydrous DCM were added Et$_3$N (4.3 mL, 30.58 mmol, 6 eq.) and TBDPSCl (7.8 mL, 30.58 mmol, 6 eq.). The reaction mixture was heated to reflux overnight and then, was washed with a 0.2 N HCl solution (2×50 mL), a saturated NaHCO$_3$ solution (100 mL) and brine (100 mL). The organic layer was dried over MgSO$_4$, filtered and evaporated under vacuum. The residue was dissolved in anhydrous DCM and precipitated by addition of hexanes. The precipitation with DCM/hexanes was repeated to get rid of excess TBDPSCl. The solids were filtered and dried under vacuum to give 2.09 g of product. (65% yield). $^1$H NMR (300 MHz, CDCl$_3$): δ 0.90 (3 H, t, J=7.6 Hz), 1.01 (3 H, t, J=7.3 Hz), 1.17 (9H, s), 1.83-1.92 (2H, m), 2.64 (2H, q, 6.9 Hz), 3.89 (1 H, s, OH), 5.11 (2H, s), 5.27 (1H, d, J=16.1 Hz), 5.72 (1H, d, J=16.4 Hz), 7.07 (2 H, d, J=2.63 Hz), 7.36-7.49 (7 H, m), 7.58 (1 H, s), 7.75-7.79 (4H, m), 8.05 (1 H, d, J=9.4 Hz). $^{13}$C NMR (75.4 MHz, CDCl$_3$): δ 7.82, 13.28, 19.52, 22.86, 26.48, 31.52, 49.23, 66.25, 72.69, 97.25, 110.09, 117.57, 125.67, 126.57, 127.65, 127.81, 130.02, 131.69, 131.97, 135.26, 143.51, 145.05, 147.12, 149.55, 149.92, 154.73, 157.43, 173.72.

Example 4

TBDPS-(10)-(7-ethyl-10-hydroxycamptothecin)-(20)-Gly-Boc (Compound 6)

To a 0° C. solution of TBDPS-(10)-(7-ethyl-10-hydroxycamptothecin) (compound 5, 3.78 g, 5.99 mmol, 1 eq.) and Boc-Gly-OH (1.57 g, 8.99 mmol, 1.5 eq.) in 100 mL of anhydrous DCM was added EDC (1.72 g, 8.99 mmol, 1.5 eq.) and DMAP (329 mg, 2.69 mmol, 0.45 eq.). The reaction mixture was stirred at 0° C. until HPLC showed complete disappearance of the starting material (approx. 1 hour and 45 minutes). The organic layer was washed with a 0.5% NaHCO$_3$ solution (2×50 mL), water (1×50 mL), a 0.1 N HCl solution (2×50 mL) and brine (1×50 mL); and dried over MgSO$_4$. After filtration and evaporation under vacuum, 4.94 g of crude product were obtained (quantitative yield). The crude solid was used in the next reaction without further purification. $^1$H NMR (300 MHz, CDCl$_3$): δ 0.89 (3 H, t, J=7.6 Hz), 0.96 (3 H, t, J=7.5 Hz), 1.18 (9H, s), 1.40 (9H, s), 2.07-2.29 (3H, m), 2.64 (2H, q, 7.5 Hz), 4.01-4.22 (2H, m), 5.00 (1 H, br s), 5.01 (2H, s), 5.37 (1H, d, J=17.0 Hz), 5.66 (1H, d, J=17.0 Hz), 7.08 (1 H, d, J=2.34 Hz), 7.16 (1H, s), 7.37-7.50 (7 H, m), 7.77 (4H, d, J=7.6 Hz), 8.05 (1 H, d, J=9.4 Hz). $^{13}$C NMR (75.4 MHz, CDCl$_3$): δ 7.52, 13.30, 19.50, 22.86, 26.45, 28.21, 31.64, 42.28, 49.14, 67.00, 76.65, 79.96, 95.31, 110.13, 118.98, 125.75, 126.45, 127.68, 127.81, 130.03, 131.54, 131.92, 135.25, 143.65, 144.91, 145.19, 147.08, 149.27, 154.75, 155.14, 157.10, 166.98, 169.17.

Example 5

TBDPS-(10)-(7-ethyl-10-hydroxycamptothecin)-(20)-Gly.HRC (Compound 7)

To a solution of TBDPS-(10)-(7-ethyl-10-hydroxycamptothecin)-(20)-Gly-Boc (compound 6, 1 g, 1.27 mmol) in 5 mL anhydrous dioxane was added 5 mL of a 4 M solution of HCl in dioxane. The reaction mixture was stirred at room temperature until HPLC showed complete disappearance of the starting material (1 hour). The reaction mixture was added to 50 mL of ethyl ether and the resulting solid was filtered. The solid was dissolved in 50 mL DCM and washed with brine (pH was adjusted to 2.5 by addition of a saturated $NaHCO_3$ solution). The organic layer was dried over $MgSO_4$, filtered and evaporated under vacuum. The residue was dissolved in 5 mL of DCM and precipitated by addition of 50 mL ethyl ether. Filtration afforded 770 mg (84% yield) final product. $^1$H NMR (300 MHz, $CDCl_3$): δ 0.84 (3 H, t, J=7.6 Hz), 1.05 (3 H, t, J=7.3 Hz), 1.16 (9H, s), 2.15-2.30 (3H, m), 2.59 (2H, q, 7.6 Hz), 4.16 (1H, d, J=17.9 Hz), 4.26 (1H, d, J=17.9 Hz), 5.13 (2H, s), 5.46 (1H, d, J=17.0 Hz), 5.60 (1H, d, J=17.0 Hz), 7.11 (1 H, d, J 2.34 Hz), 7.30 (1H, s), 7.40-7.51 (6 H, m), 7.56 (1H, dd, J=2.34, 9.4 Hz), 7.77 (4H, dd, J=7.6, 1.6 Hz), 7.98 (1 H, d, J=9.1 Hz). $^{13}$C NMR (75.4 MHz, $CDCl_3$): δ 8.09, 13.72, 20.26, 23.61, 26.94, 31.83, 41.01, 50.71, 67.62, 79.51, 97.03, 111.65, 119.69, 127.13, 128.97, 128.99, 129.11, 131.43, 131.96, 133.00, 133.03, 136.51, 145.62, 145.81, 147.24, 148.29, 150.58, 156.27, 158.68, 167.81, 168.34.

Example 6

$^{40k}$4arm-PEG-Gly-(20)-(7-ethyl-10-hydroxycamptothecin)-(10) -TBDPS (Compound 8)

To a solution of $^{40k}$4arm-PEGCOOH (compound 3, 1.4 g, 0.036 mmol, 1 eq.) in 14 mL of anhydrous DCM was added TBDPS-(10)-(7-ethyl-10-hydroxycamptothecin)-(20) -Gly. HCl (compound 7, 207 mg, 0.29 mmol, 2.0 eq. per active site), DMAP (175 mg, 1.44 mmol, 10 eq.) and PPAC (0.85 mL of a 50% solution in EtOAc, 1.44 mmol, 10 eq.). The reaction mixture was stirred at room temperature overnight and then, evaporated under vacuum. The resulting residue was dissolved in DCM and the product was precipitated with ether and filtered. The residue was recrystallized with DMF/IPA to give the product (1.25 g). $^{13}$C NMR (75.4 MHz, $CDCl_3$): δ 7.45, 13.20, 19.39, 22.73, 26.42, 31.67, 40.21, 49.01, 66.83, 95.16, 110.02, 118.83, 125.58, 126.40, 127.53, 127.73, 129.96, 131.49, 131.76, 131.82, 135.12, 143.51, 144.78, 145.13, 146.95, 149.21, 154.61, 156.92, 166.70, 168.46, 170.30.

Example 7

$^{40k}$4arm-PEG-Gly(20)-(7-ethyl-10-hydroxycamptothecin) (Compound 9)

To compound $^{40k}$4arm-PEG-Gly-(20)-(7-ethyl-10-hydroxycamptothecin) -(10)-TB DPS (compound 8, 1.25 g) was added a solution of TBAF (122 mg, 0.46 mmol, 4 eq.) in a 1:1 mixture of THF and a 0.05 M HCl solution (12.5 mL). The reaction mixture was stirred at room temperature for 4 hours and then, extracted with DCM twice. The combined organic phases were dried over $MgSO_4$, filtered and evaporated under vacuum. The residue was dissolved in 7 mL of DMF and precipitated with 37 mL IPA. The solid was filtered and washed with IPA. The precipitation with DMF/IPA was repeated. Finally the residue was dissolved in 2.5 mL of DCM and precipitated by addition of 25 mL of ether. The solid was filtered and dried at 40° C. in vacuum oven overnight (860 mg). $^{13}$C NMR (75.4 MHz, $CDCl_3$): δ 7.48, 13.52, 22.91, 31.67, 40.22, 49.12, 66.95, 94.82, 105.03, 118.68, 122.54, 126.37, 128.20, 131.36, 142.92, 144.20, 144.98, 147.25, 148.29, 156.44, 156.98, 166.82, 168.49, 170.39. This NMR data shows no sign of PEG-COOH which indicates that all of the COOH reacted. The loading, as determined by fluorescence detection was found to be 3.9 which is consistent with fall loading of the 7-ethyl-10-hydroxycamptothecin on each of the four branches of the polymer. Repeated runs of this experiments at much larger scale yielded consistent results.

Biological Data

Example 8

Toxicity Data

A maximum tolerated dose (MTD) of four-arm PEG conjugated 7-ethyl-10-hydroxycamptothecin was studied using nude mice. Mice were monitored for 14 days for mortality and signs of illness and sacrificed when body weight loss was >20% of the pretreatment body weight.

Table 1 shows the maximum tolerated dose of compound 9 for both single dose and multiple dose administration. Each dose for multiple dose administration was given mice every other day for 10 days and the mice were observed for another 4 days, thus for total 14 days.

TABLE 1

MTD Data in Nude Mice

| Compound | Dose Level (mg/kg) | Survival/Total | Comments |
| --- | --- | --- | --- |
| Compound 9 Single dose | 25 | 5/5 | |
| | 30 | 5/5 | |
| | 35 | 4/5 | Mouse euthanized due to >20% body weight loss |
| Compound 9 Multiple dose | 10 | 5/5 | |
| | 15 | 3/5 | Mice euthanized due to >20% body weight loss |
| | 20 | 0/5 | Mice euthanized due to >20% body weight loss |

The MTD found for 4arm-PEG-Gly-(7-ethyl-10-hydroxycamptothecin) (compound 9) was 3 0 mg/kg when given as single dose, and 10 mg/kg when given as multiple dose (q2d× 5).

Example 9

Cytotoxicity in Non-Hodgkin's Lymphoma Cells

The cytotoxicity provides an indication of the in vitro anti-tumor potency of each compound. The in vitro cytotoxicity of PEG-Gly-(7-ethyl-10-hydroxycamptothecin) (compound 9) and CPT-11 was determined using a MTS assay. Cells were incubated with drugs for 72 hours at 37° C. Following incubation, MTS dye was added and formation of a colored product (formazan) was measured at 490 nm.

The $IC_{50}$ values of compound 9 and CPT-11 indicate that compound 9 has much higher in vitro inhibition in the tested NHL cells than CPT-11. The IC 50 of compound 9 ranged between 2 and 20 nM in the Raji and Daudi Burkitt's lymphoma cells and was about 30 to 50 fold more potent than CPT-11.

Example 10

In Vitro Metabolism

Figure 3:
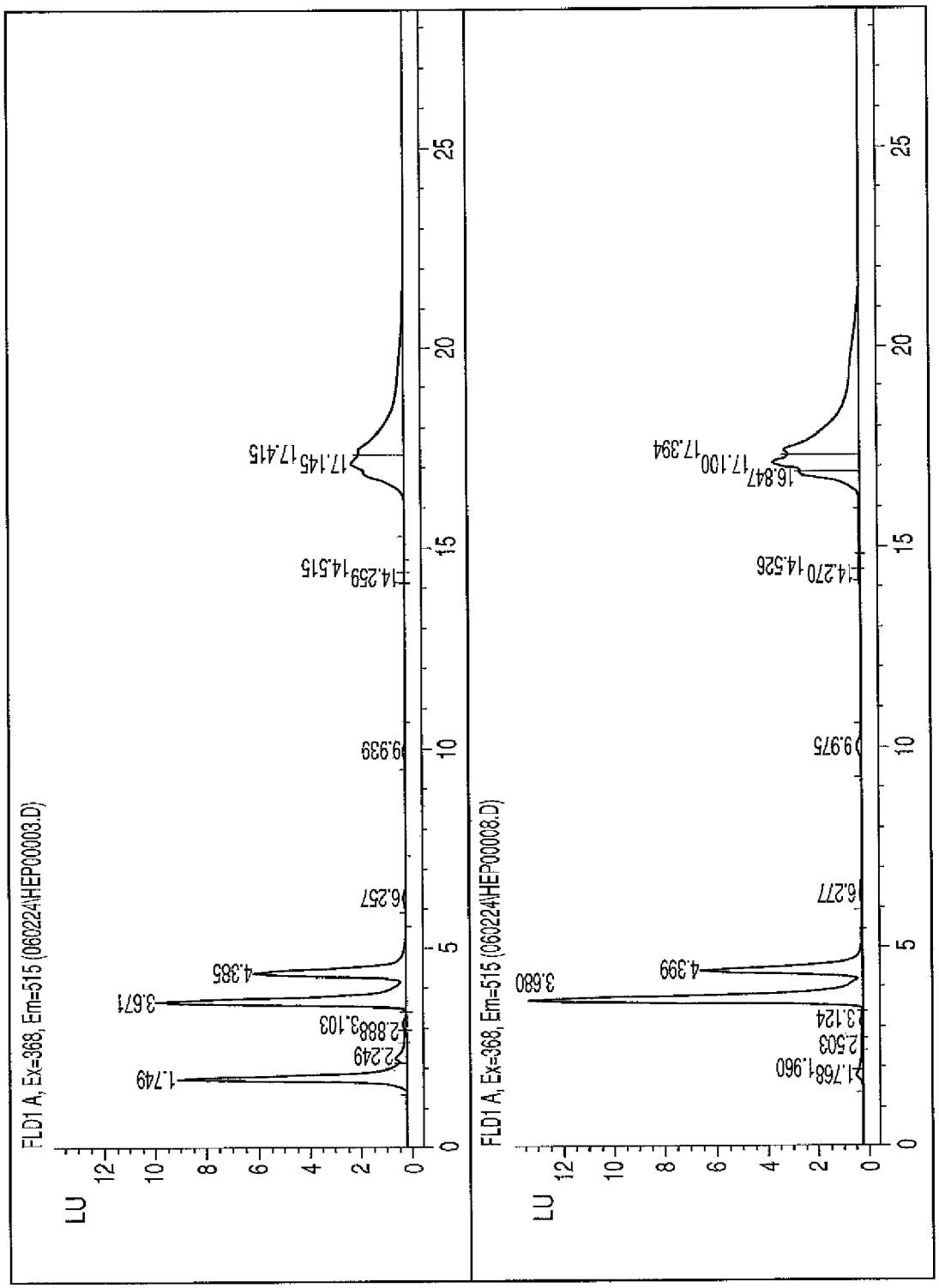
FIG. 3 shows in vitro metabolism of 4arm-PEG-Gly-(7-ethyl-10-hydroxycamptothecin) as described in Example 10.

In vitro metabolism of PEG-Gly-(7-ethyl-10-hydroxycamptothecin) conjugates (compound 9) was observed in rat hepatocytes. Compound 9 was incubated with rat hepatocytes for 2 hours, pH 7.5, 37° C. As shown in FIG. 3, 7-ethyl-10-hydroxy-camptothecin and 7-ethyl-10-hydroxycamptothecin-Glueuronide (7-ethyl-10-hydroxy-camptothecin-G) were the major metabolites identified, which agrees with known metabolic pathway of 7-ethyl-10-hydroxycamptothecin in vivo.

Example 11

Properties of PEG Conjugates

Table 2 shows solubility of PEG-(7-ethyl-10-hydroxycamptothecin) conjugates in aqueous saline solution. Compound 9 showed good solubility of up to 4 mg/mL equivalent of 7-ethyl-10-hydroxycamptothecin. In human plasma, 7-ethyl-10-hydroxycamptothecin was steadily released from the PEG conjugates with a doubling time of 22 to 52 minutes and the release appeared to be pH and concentration dependent as described in the following Example 12

TABLE 2

Properties of PEG-7-ethyl-10-hydroxycamptothecin Conjugates

| Compound | Solubility in Saline (mg/mL)$^a$ | $t_{1/2}$(min) in Human Plasma$^b$ | Doubling Time in Plasma (min)$^c$ | | |
|---|---|---|---|---|---|
| | | | Human | Mouse | Rat |
| Compound 9 (Gly) | 180 | 12.3 | 31.4 | 49.5 | 570 |

$^a$7-ethyl-10-hydroxycamptothecin is not soluble in saline.
$^b$PEG conjugate half life.
$^c$7-ethyl-10-hydroxycamptothecin formation rate from conjugates.

PEG-Gly-7-ethyl-10-hydroxycamptothecin conjugates show good stability in saline and other aqueous medium for up to 24 hours at room temperature.

Example 12

Effects of Concentration and pH on Stability

The aqueous stability and hydrolysis properties in rat and human plasma were monitored using U based HPLC methods. 4arm PEG-Gly-(7-ethyl-10-hydroxycamptothecin) conjugates (compound 9) were incubated with each sample for 5 minutes at room temperature.

Figure 4:
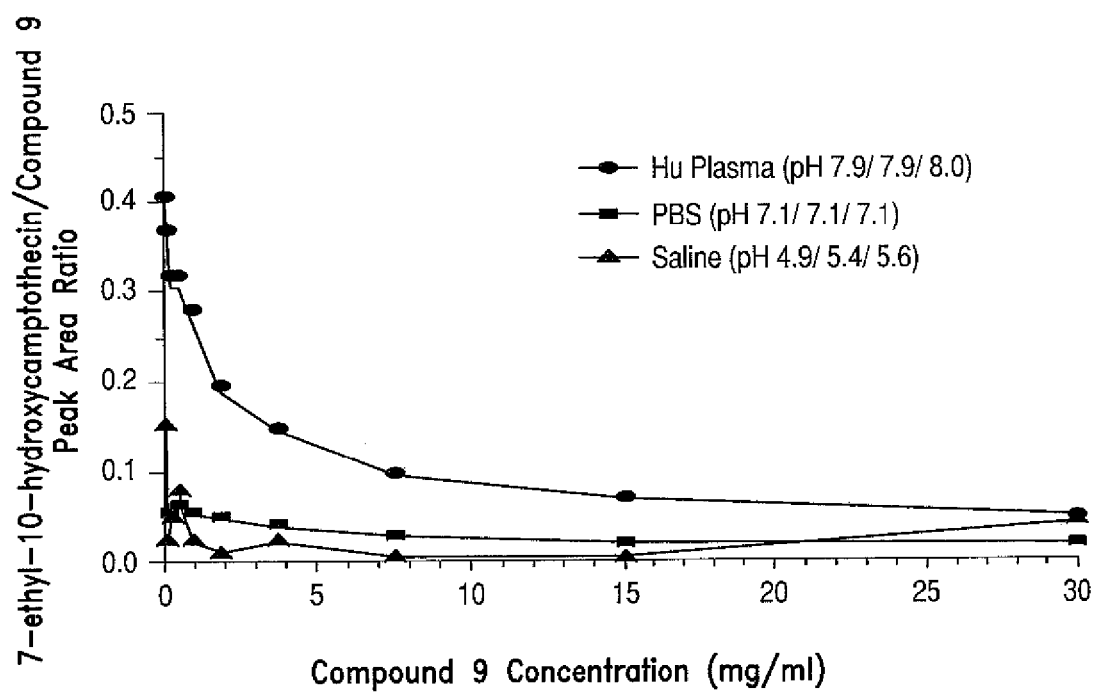
FIG. 4 shows stability of 4arm-PEG-Gly-(7-ethyl-10-hydroxycamptothecin) as described in Example 12.
Figure 5:
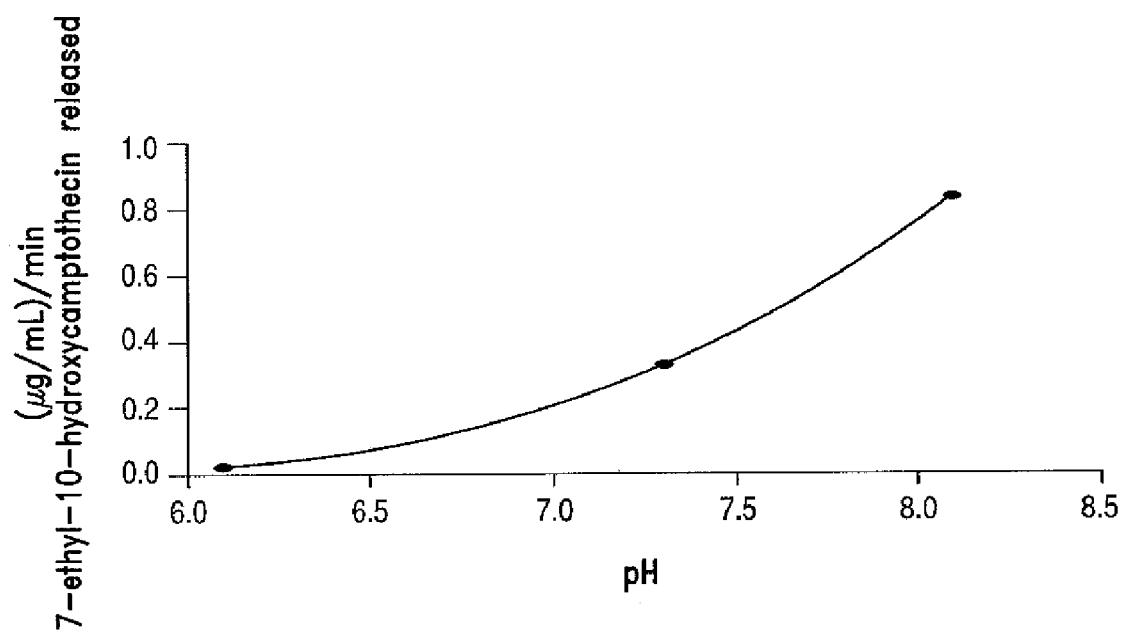
FIG. 5 shows effect of pH on stability of 4arm-PEG-Gly-(7-ethyl-10-hydroxycamptothecin) as described in Example 12.

Stability of PEG-7-ethyl-10-hydroxycamptothecin conjugates in buffer was pH dependent. FIG. 4 shows 4arm PEG-Gly-(7-ethyl-10-hydroxycamptothecin) stability in various samples. FIG. 5 shows that rate of 7-ethyl-10-hydroxycamptothecin release from PEG-Gly-(7-ethyl-10-hydroxycamptothecin) increases with increased pH.

Example 13

Pharmacokinetics

Tumor free Balb/C mice were injected with a single injection of 20 mg/kg 4arm PEG-Gly-(7-ethyl-10-hydroxycamptothecin) conjugates. At various time points mice were sacrificed and plasma was analyzed for intact conjugates and released 7-ethyl-10-hydroxy-camptothecin by HPLC. Pharmacokinetic analysis was done using non-compartmental analysis (WinNonlin). Details are set forth in Table 3.

TABLE 3

Pharmacokinetic Data

| Parameter | Compound 9 | 7-ethyl-10-hydroxy-camptothecin Released from Compound 9 |
|---|---|---|
| AUC (h*μg/mL) | 124,000 | 98.3 |
| Terminal $t_{1/2}$ (Hr) | 19.3 | 14.2 |
| $C_{max}$ (μg/mL) | 20,500 | 13.2 |
| CL (mL/hr/kg) | 5.3 | 202 |
| Vss (mL/kg) | 131 | 3094 |

Figure 6:
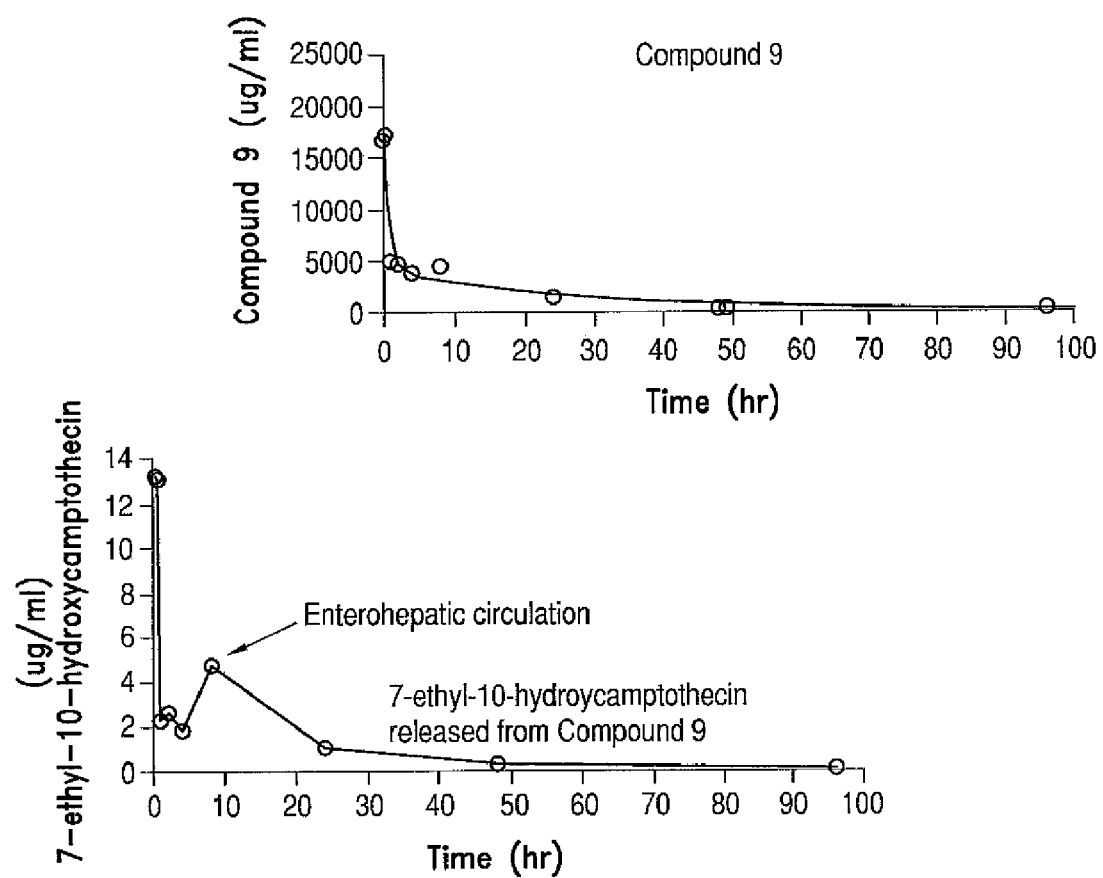
FIG. 6 shows pharmacokinetic profiles of 4arm-PEG-Gly-(7-ethyl-10-hydroxy-camptothecin) as described in Example 13.

As shown in FIG. 6, pegylation of 7-ethyl-10-hydroxycamptothecin allows long circulation half life and high exposure to native drug 7-ethyl-10-hydroxycamptothecin. Enterohepatic circulation of 4arm PEG-Gly-(7-ethyl-10-hydroxycamptothecin) conjugates was observed. The pharmacokinetic profile of PEG-Gly-(7-ethyl-10-hydroxycamptothecin) in mice was biphasic showing a rapid plasma distribution phase during the initial 2 hours followed by a 18-22 hours terminal elimination half-life for the conjugate and a concomitant 18-26 hours terminal elimination half-life for 7-ethyl-10-hydroxycamptothecin.

Additionally, pharmacokinetic profiles of 4arm PEG-Gly-(7-ethyl-10-hydroxy-camptothecin) were investigated in rats. In rats, does levels of 3, 10 and 30 mg/kg (7-ethyl-10-hydroxycamptothecin equivalent) were used. The pharmacokinetic profiles in rats were consistent with those of mice.

In rats, 4arm PEG-Gly-(7-ethyl-10-hydroxycamptothecin) showed a biphasic clearance from the circulation with an elimination half life of 12-18 hours in rats. 7-ethyl-10-hydroxycamptothecin released from 4arm PEG-Gly-7-ethyl-10-hydroxycamptothecin conjugates had an apparent elimination half life of 21-22 hours. The maximum plasma concentration ($C_{max}$) and area under the curve (AUC) increased in a dose dependent manner in rats. The apparent halflife of released 7-ethyl-10-hydroxycamptothecin from 4arm PEG-Gly conjugates in mice or rats is significantly longer than the reported apparent half life of released 7-ethyl-10-hydroxycamptothecin from CPT-11 and the exposure of released 7-ethyl-10-hydroxycamptothecin from 4arm PEG-Gly-(7-ethyl-10-hydroxycamptothecin) is significantly higher than the reported exposure of released 7-ethyl-10-hydroxycamptothecin from CPT-11. The clearance of the parent compound was 0.35 mL/hr/kg in rats. The estimated volume of distribution at steady state (Vss) of the parent compound was 5.49 mL/kg. The clearance of the released 7-ethyl-10-hydroxycamptothecin was 131 mL/hr/kg in rats. The estimated Vss of released 7-ethyl-10-hydroxycamptothecin was 2384 mL/kg in rats. Enterohepatic circulation of released 7-ethyl-10-hydroxycamptothecin was observed both in mice and rats.

Example 14

In Vivo DATA-Efficacies in Raji Human Burkitt's Lymphoma Xenografted Mice Model The antitumor efficacy of compound 9 of Example 7 was measured in Raji Burkitt's lymphoma xenografted mice. Disseminated xenograft tumors were established in SCID CB17 mice by injecting $2.5 \times 10^6$ human Burkitt's lymphoma cells (Raji) intravenously. The mice were then randomly assigned to each test group (10 mice per group). 30 mg/kg body weight of compound 9 was injected intravenously as a single dose at day 1 in the group treated with compound 9. In the mice treated with CPT-11, 60 mg/kg body weight of CPT-11 was injected. Therapy was initiated 1 day post injection of cells.

In multiple dose regimen treatment, 10 mg/kg of compound 9 and 40 mg/kg of CPT-11 was injected intravenously at q2d×5 for each group. Control group received saline.

In all aspects, the amount of compound 9 administered is based on the amount of 7-ethyl-10-hydroxycamptothecin, not the amount of polymeric conjugate administered.

The animals were monitored daily for any signs of illness, general behavioral changes and survival. Body weight was also monitored. Mice bearing tumors that showed open necrotic lesions were sacrificed. Mice losing more than 20% of body weight were also humanely sacrificed. For all the treatment groups, mice were monitored for tumor growth and survival. All mice were euthanized by $CO_2$ inhalation at the termination of study. The results of cure rate and increased life span (ILS) are set forth in Table 4.

TABLE 4

| | Therapeutic Efficacies | | | |
| | Single Dose Treatment | | Multiple Dose Treatment | |
| Group | Cure (%) | ILS (%) | Cure (%) | ILS (%) |
|---|---|---|---|---|
| Compound 9 | 50 | 500 | 90 | — |
| CPT-11 | 0 | 19 | 0 | 63 |

The results show that the mice treated with compound 9 had 50% cure rate in the single dose treatment. The mice treated with compound 9 showed 90% in the multiple dose treatment. None of the mice treated with CPT-11 were cured in either single dose or multiple dose treatment. For purposes of Examples, "cure" is understood to mean there are no signs of tumor by gross observation 100 days after completion of treatment.

The results indicate that compounds described herein have utility in treating patients with non-Hodgkin's lymphomas such as Burkitt's lymphoma. The results also indicate that the compounds described in can be an alternative to therapy based on CPT-11.

Example 15

In Vivo DATA-Efficacies in Daudi Human Burkitt's Lymphoma Xenografted Mice Model The antitumor efficacy of compound 9 was also measured in Daudi Burkitt's lymphoma xenografted mice. Disseminated xenograft tumors were established in SCID CB17 mice by injecting $2.5 \times 10^6$ human Burkitt's lymphoma cells (Daudi) intravenously. The mice were then randomly assigned to each test group (10 mice per group). Early treatment therapy was initiated 1 day post injection of tumor cells. Delayed treatment was initiated 7 days after injection of tumor cells.

30 mg/kg body weight of compound 9 was injected intravenously as a single dose at day 1 (early treatment) or day 7 (delayed treatment) in the group treated with compound 9. In the mice treated with CPT-11, 60 mg/kg body weight of CPT-11 was injected. The control group of mice received saline.

The animals were monitored daily for any signs of illness, general behavioral changes and survival. Body weight was also monitored. Mice bearing tumors that showed open necrotic lesions were sacrificed. Mice losing more than 20% of body weight were also humanely sacrificed. For all the treatment groups, mice were monitored for tumor growth and survival. All mice were euthanized by $CO_2$ inhalation at the termination of study. The results of cure rate and increase life span (ILS) are set forth in Table 5.

TABLE 5

| | Therapeutic Efficacies | | | |
| | Single Dose-Early Treatment | | Single Dose-Delayed Treatment | |
| Group | Cure (%) | ILS (%) | Cure (%) | ILSI (%) |
|---|---|---|---|---|
| Compound 9 | 100 | — | 90 | — |
| CPT-11 | 0 | 66 | 0 | 0 |

In the single dose early treatment group, the mice treated with compound 9 had 100% cure rate. The mice treated with compound 9 also showed 90% cure rate in the delayed treatment single dose treatment. None of the mice treated with CPT-11 were cured. The results indicate that the compounds described herein have utility in treating patients with non-Hodgkin's lymphomas in various stages of non-Hodgkin's lymphomas.

I claim:

1. A method of treating a mammal having a non-Hodgkin's lymphoma, comprising administering an effective amount of a compound of the formula

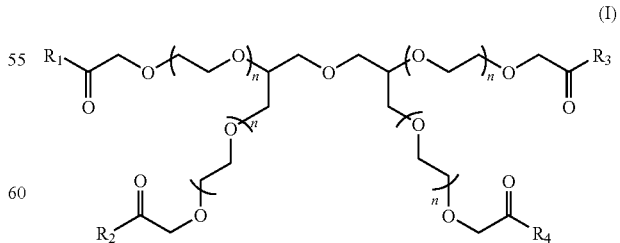

wherein $R_1$, $R_2$, $R_3$ and $R_4$ are independently OH or $(L)_m$-D;

L is a bifunctional linker;

D is

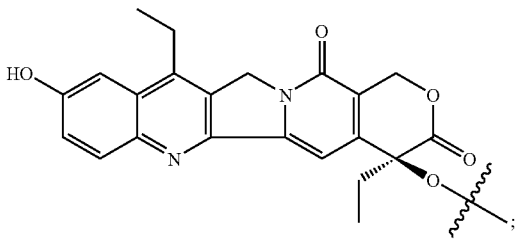

m is 0 or a positive integer; and
n is a positive integer;
provided that $R_1$, $R_2$, $R_3$ and $R_4$ are not all OH;
to a mammal in need thereof; wherein the non-Hodgkin's lymphoma is a Burkitt's lymphoma or a follicular lymphoma.

2. The method of claim 1, wherein the amount administered is from about 0.3 mg/m² body surface/dose to about 90 mg/m² body surface/dose.

3. The method of claim 2, wherein the amount administered is from about 0.9 mg/m² body surface/dose to about 30 mg/m² body surface/dose.

4. The method of claim 1, wherein the amount is administered according to a protocol of from about 1 mg/m² body surface/dose to about 16 mg/m² body surface/dose given weekly for three weeks, followed by 1 week without treatment and repeating for about 3 cycles.

5. The method of claim 4, wherein the amount administered per every three weeks is from about 1.25 mg/m² body surface/dose to about 45 mg/m² body surface/dose.

6. The method of claim 1, wherein L is an amino acid or amino acid derivative, wherein the amino acid derivative is selected from the group consisting of 2-aminoadipic acid, 3-aminoadipic acid, beta-alanine, beta-aminopropionic acid, 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4-aminobutyric acid, desmosine, 2,2-diaminopimelic acid, 2,3-diaminopropionic acid, n-ethylglycine, N-ethylasparagine, 3-hydroxyproline, 4-hydroxyproline, isodesmosine, allo-isoleucine, N-methylglycine, sarcosine, N-methyl-isoleucine, 6-N-methyl-lysine, N-methylvaline, norvaline, norleucine, and ornithine.

7. The method of claim 6, wherein L is glycine, alanine, methionine or sarcosine.

8. The method of claim 6 wherein L is glycine.

9. The method of claim 1, wherein L is selected from the group consisting of

—[C(=O)]$_v$(CR$_{22}$R$_{23}$)$_t$—,
—[C(=O)]$_v$(CR$_{22}$R$_{23}$)$_t$—O—,
—[C(=O)]$_v$(CR$_{22}$R$_{23}$)$_t$—NR$_{26}$—,
—[C(=O)]$_v$O(CR$_{22}$R$_{23}$)$_t$—,
—[C(=O)]$_v$O(CR$_{22}$R$_{23}$)$_t$O—,
—[C(=O)]$_v$O(CR$_{22}$R$_{23}$)$_t$NR$_{26}$—,
—[C(=O)]$_v$NR$_{21}$(CR$_{22}$R$_{23}$)$_t$—,
—[C(=O)]$_v$NR$_{21}$(CR$_{22}$R$_{23}$)$_t$O—,
—[C(=O)]$_v$NR$_{21}$(CR$_{22}$R$_{23}$)$_t$NR$_{26}$—,
—[C(=O)]$_v$(CR$_{22}$R$_{23}$O)$_t$—,
—[C(=O)]$_v$O(CR$_{22}$R$_{23}$O)$_t$—,
—[C(=O)]$_v$NR$_{21}$(CR$_{22}$R$_{23}$O)$_t$—,
—[C(=O)]$_v$(CR$_{22}$R$_{23}$O)$_t$(CR$_{24}$R$_{25}$)$_y$—,
—[C(=O)]$_v$O(CR$_{22}$R$_{23}$O)$_t$(CR$_{24}$R$_{25}$)$_y$—,
—[C(=O)]$_v$NR$_{21}$(CR$_{22}$R$_{23}$O)$_t$(CR$_{24}$R$_{25}$)$_y$—,
—[C(=O)]$_v$(CR$_{22}$R$_{23}$O)$_t$(CR$_{24}$R$_{25}$)$_y$O—,
—[C(=O)]$_v$(CR$_{22}$R$_{23}$)$_t$(CR$_{24}$R$_{25}$O)$_y$—,
—[C(=O)]$_v$O(CR$_{22}$R$_{23}$O)$_t$(CR$_{24}$R$_{25}$)$_y$O—,
—[C(=O)]$_v$O(CR$_{22}$R$_{23}$)$_t$(CR$_{24}$R$_{25}$O)$_y$—,
—[C(=O)]$_v$NR$_{21}$(CR$_{22}$R$_{23}$O)$_t$(CR$_{24}$R$_{25}$)$_y$O—,
—[C(=O)]$_v$NR$_{21}$(CR$_{22}$R$_{23}$)$_t$(CR$_{24}$R$_{25}$O)$_y$—,
—[C(=O)]$_v$(CR$_{22}$R$_{23}$)$_t$O—(CR$_{28}$R$_{29}$)$_{t'}$—,
—[C(=O)]$_v$(CR$_{22}$R$_{23}$)$_t$NR$_{26}$—(CR$_{28}$R$_{29}$)$_{t'}$—,
—[C(=O)]$_v$(CR$_{22}$R$_{23}$)$_t$S—(CR$_{28}$R$_{29}$)$_{t'}$—,
—[C(=O)]$_v$O(CR$_{22}$R$_{23}$)$_t$O—(CR$_{28}$R$_{29}$)$_{t'}$—,
—[C(=O)]$_v$O(CR$_{22}$R$_{23}$)$_t$NR$_{26}$—(CR$_{28}$R$_{29}$)$_{t'}$—,
—[C(=O)]$_v$O(CR$_{22}$R$_{23}$)$_t$S—(CR$_{28}$R$_{29}$)$_{t'}$—,
—[C(=O)]$_v$NR$_{21}$(CR$_{22}$R$_{23}$)$_t$O—(CR$_{28}$R$_{29}$)$_{t'}$—,
—[C(=O)]$_v$NR$_{21}$(CR$_{22}$R$_{23}$)$_t$NR$_{26}$—(CR$_{28}$R$_{29}$)$_{t'}$—,
—[C(=O)]$_v$NR$_{21}$(CR$_{22}$R$_{23}$)$_t$S—(CR$_{28}$R$_{29}$)$_{t'}$—,
—[C(=O)]$_v$(CR$_{22}$R$_{23}$CR$_{28}$R$_{29}$O)$_t$NR$_{26}$—,
—[C(=O)]$_v$(CR$_{22}$R$_{23}$CR$_{28}$R$_{29}$O)$_t$—,
—[C(=O)]$_v$O(CR$_{22}$R$_{23}$CR$_{28}$R$_{29}$O)$_t$NR$_{26}$—,
—[C(=O)]$_v$O(CR$_{22}$R$_{23}$CR$_{28}$R$_{29}$O)$_t$—,
—[C(=O)]$_v$NR$_{21}$(CR$_{22}$R$_{23}$CR$_{28}$R$_{29}$O)$_t$NR$_{26}$—,
—[C(=O)]$_v$NR$_{21}$(CR$_{22}$R$_{23}$CR$_{28}$R$_{29}$O)$_t$—,
—[C(=O)]$_v$(CR$_{22}$R$_{23}$CR$_{28}$R$_{29}$O)$_t$(CR$_{24}$R$_{25}$)$_y$—,
—[C(=O)]$_v$O(CR$_{22}$R$_{23}$CR$_{28}$R$_{29}$)$_t$(CR$_{24}$R$_{25}$)$_y$—,
—[C(=O)]$_v$NR$_{21}$(CR$_{22}$R$_{23}$CR$_{28}$R$_{29}$O)$_t$(CR$_{24}$R$_{25}$)$_y$—,
—[C(=O)]$_v$(CR$_{22}$R$_{23}$CR$_{28}$R$_{29}$O)$_t$(CR2$_4$R$_{25}$)$_y$O—,
—[C(=O)]$_v$(CR$_{22}$R$_{23}$)$_t$(CR$_{24}$R$_{25}$CR$_{28}$R$_{29}$O)$_y$—,
—[C(=O)]$_v$(CR$_{22}$R$_{23}$)$_t$(CR$_{24}$R$_{25}$CR$_{28}$R$_{29}$O)$_y$NR$_{26}$—,
—[C(=O)]$_v$O(CR$_{22}$R$_{23}$CR$_{28}$R$_{29}$O)$_t$(CR$_{24}$R$_{25}$)$_y$O—,
—[C(=O)]$_v$O(CR$_{22}$R$_{23}$)$_t$(CR$_{24}$R$_{25}$CR$_{28}$R$_{29}$O)$_y$—,
—[C(=O)]$_v$O(CR$_{22}$R$_{23}$)$_t$(CR$_{24}$R$_{25}$CR$_{28}$R$_{29}$O)$_y$NR$_{26}$—,
—[C(=O)]$_v$NR$_{21}$(CR$_{22}$R$_{23}$CR$_{28}$R$_{29}$O)$_t$(CR$_{24}$R$_{25}$)$_y$O—,
—[C(=O)]$_v$NR$_{21}$(CR$_{22}$R$_{23}$)$_t$(CR$_{24}$R$_{25}$CR$_{28}$R$_{29}$O)$_y$—,
—[C(=O)]$_v$NR$_{21}$(CR$_{22}$R$_{23}$)$_t$(CR$_{24}$R$_{25}$CR$_{28}$R$_{29}$O)$_y$NR$_{26}$—,

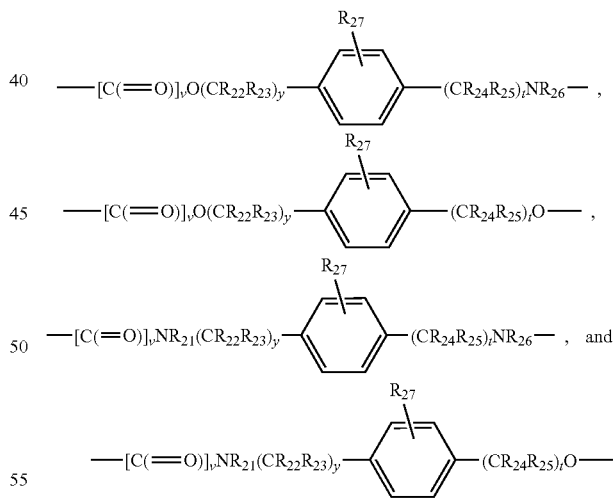

wherein:
$R_{21}$-$R_{29}$ are independently selected from the group consisting of hydrogen, amino, substituted amino, azido, carboxy, cyano, halo, hydroxyl, nitro, silyl ether, sulfonyl, mercapto, $C_{1-6}$ alkylmercapto, arylmercapto, substituted arylmercapto, substituted $C_{1-6}$ alkylthio, $C_{1-6}$ alkyls, $C_{2-6}$ alkenyl, $C_{2-6}$ alkynyl, $C_{3-19}$ branched alkyl, $C_{3-8}$ cycloalkyl, $C_{1-6}$ substituted alkyl, $C_{2-6}$ substituted alkenyl, $C_{2-6}$ substituted alkynyl, $C_{3-8}$ substitute cycloalkyl, aryl, substituted aryl, heteroaryl, substituted heteroaryl, $C_{1-6}$ heteroalkyl, substituted $C_{1-6}$ heteroalkyl, $C_{1-6}$ alkoxy, aryloxy, $C_{1-6}$ heteroalkoxy, heteroaryloxy, $C_{2-6}$ alkanoyl, arylcarbonyl, $C_{2-6}$ alkoxycarbonyl, aryloxycarbonyl, $C_{2-6}$ alkanoyloxy, arylcarbonyloxy, $C_{2-6}$ substituted alkanoyl, substituted arylcarbonyl, $C_{2-6}$ substituted alkanoyloxy, substituted aryloxycarbonyl, $C_{2-6}$ substituted alkanoyloxy, and substituted arylcarbonyloxy;

(t), (t') and (y) are independently selected from zero or a positive integer; and (v) is 0 or 1.

10. The method of claim 1, wherein m is from about 1 to about 10.

11. The method of claim 1, wherein m is about 1.

12. The method of claim 1, wherein n is from about 28 to about 341.

13. The method of claim 1, wherein n is from about 114 to about 227.

14. The method of claim 1, wherein n is about 227.

15. The method of claim 1, wherein the compound is selected from the group consisting of

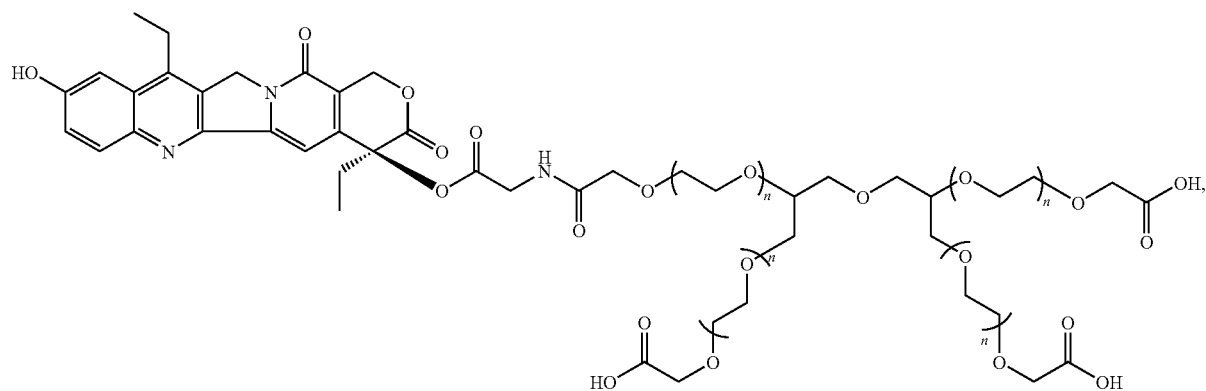

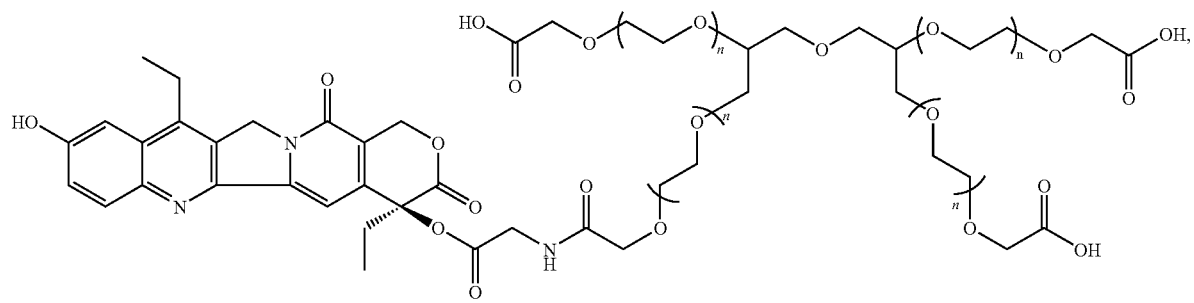

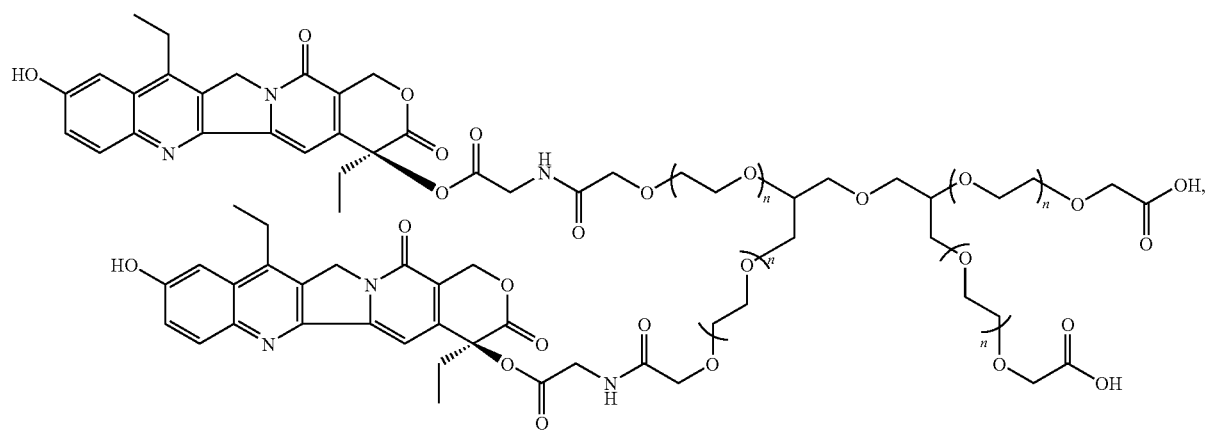

-continued
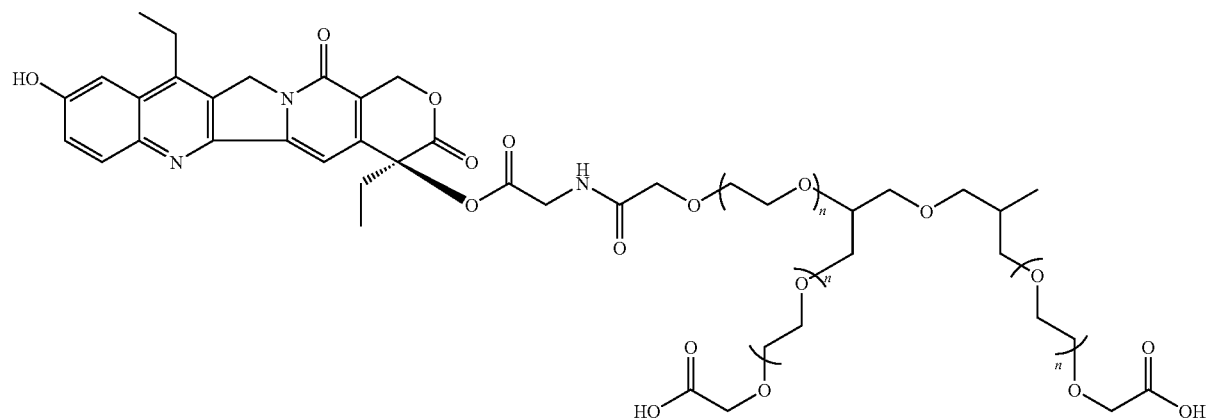
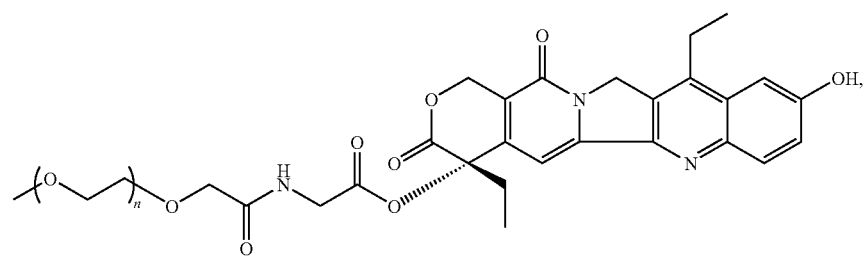
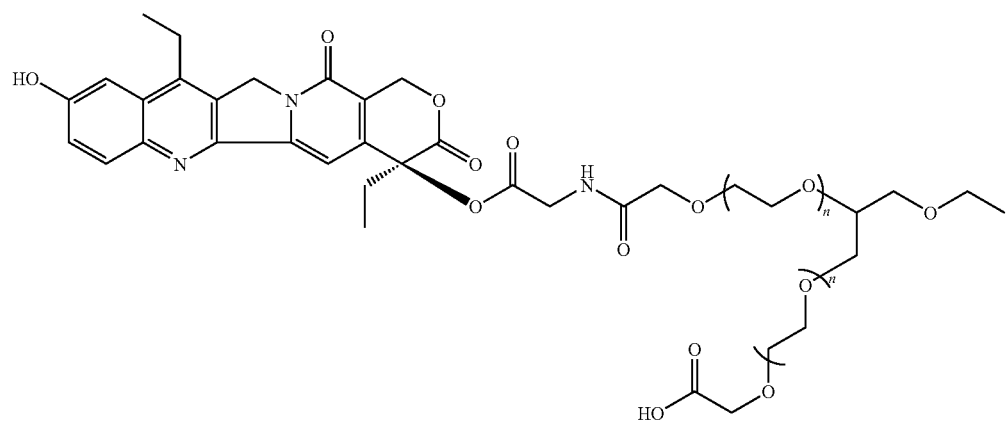
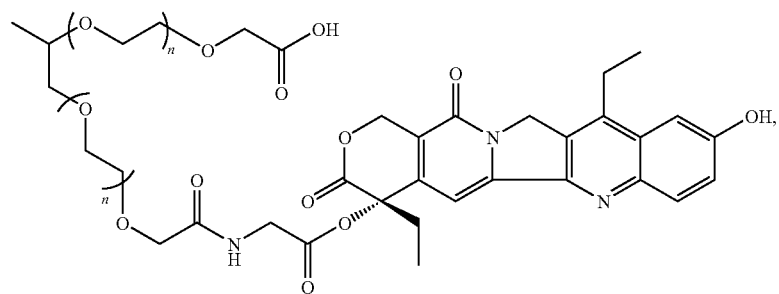

-continued
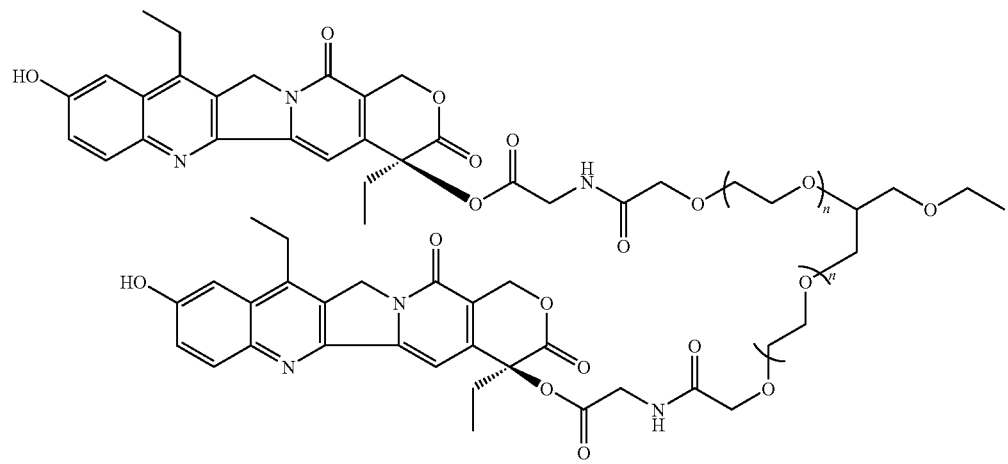
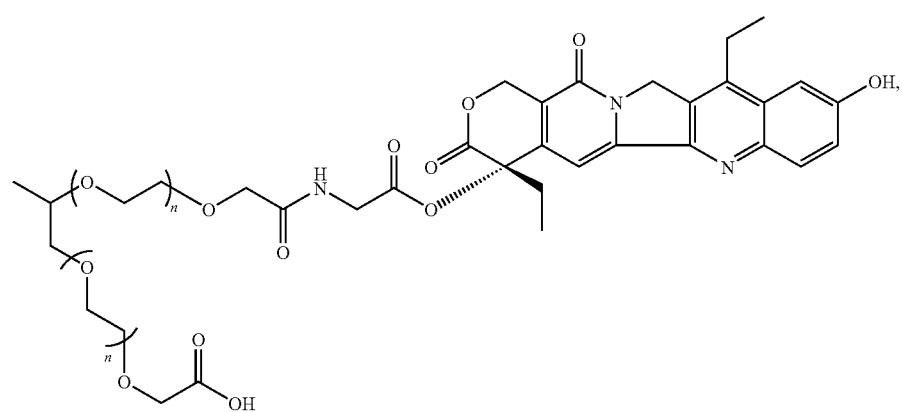
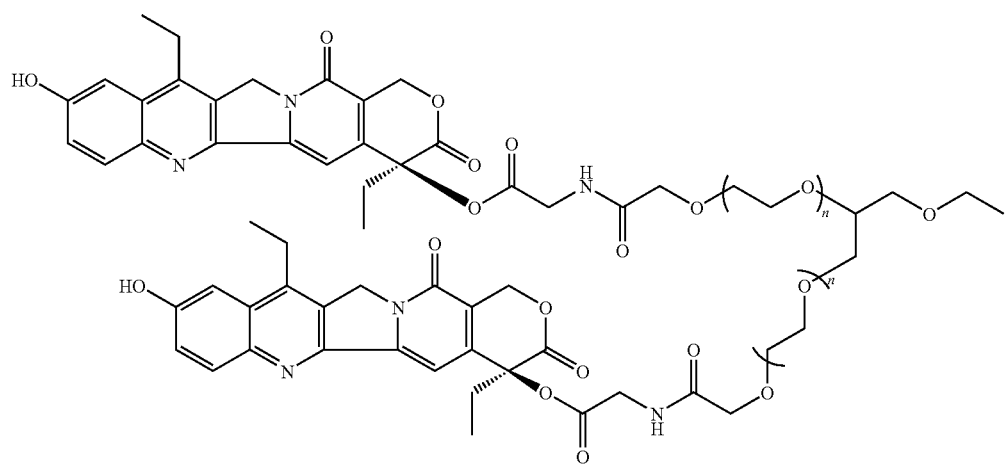
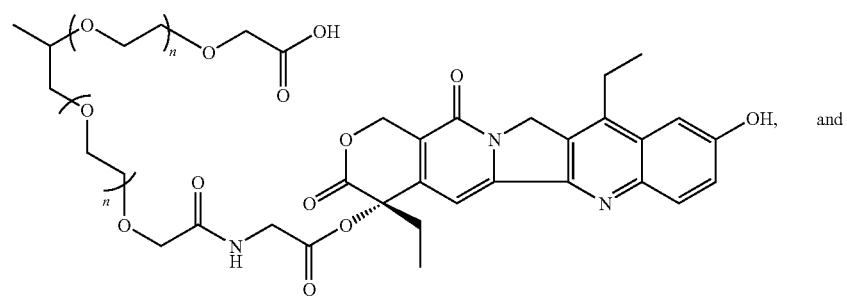

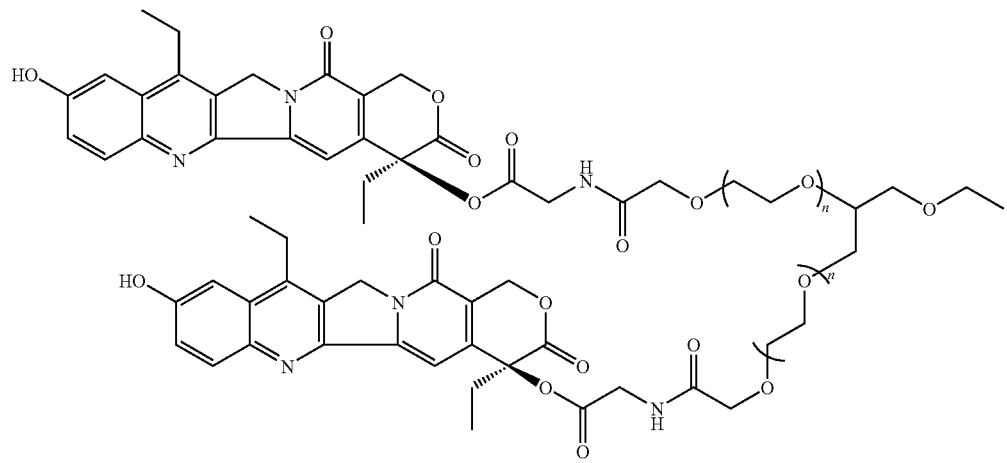
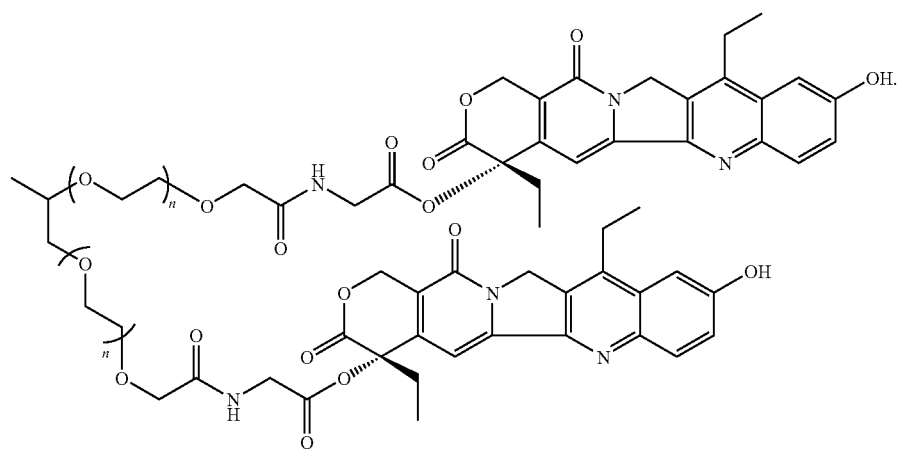
16. The method of claim 1, wherein the compound is
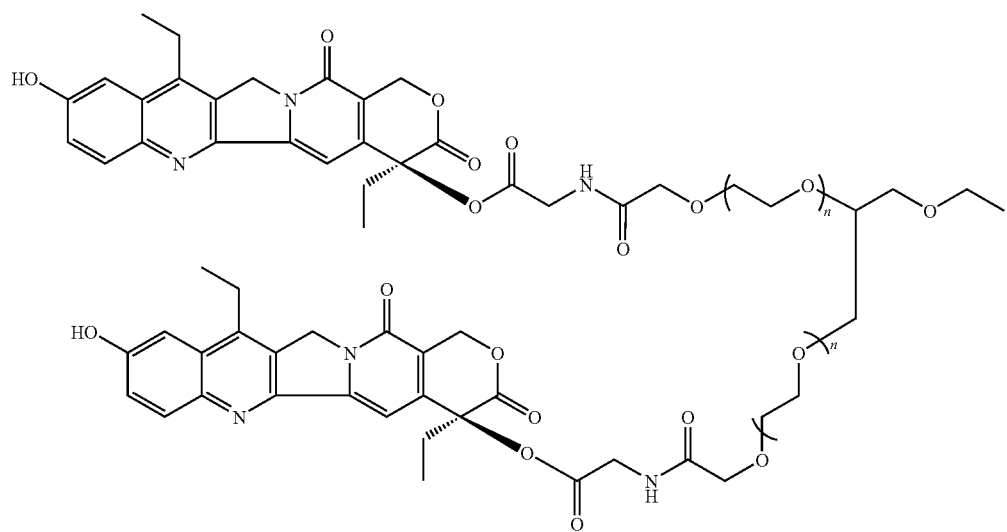

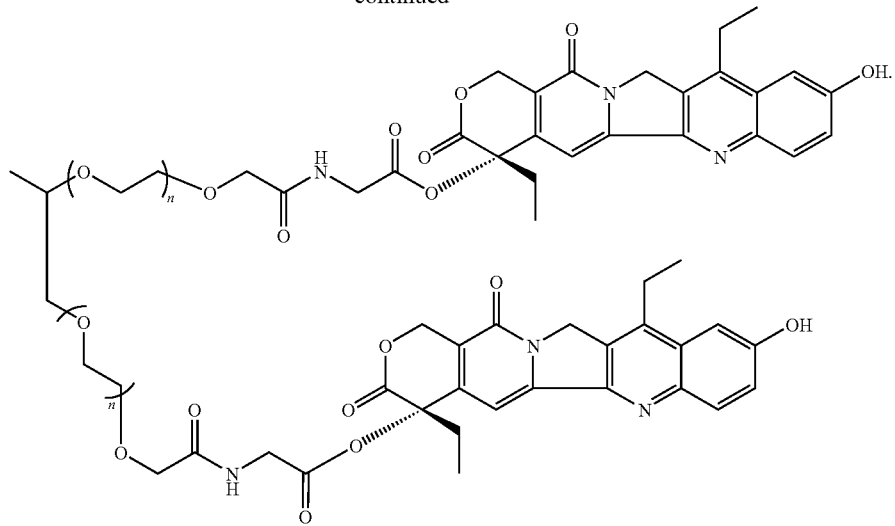
17. A method of treating a mammal having a non-Hodgkin's lymphoma, comprising administering an effective amount of a compound having the formula
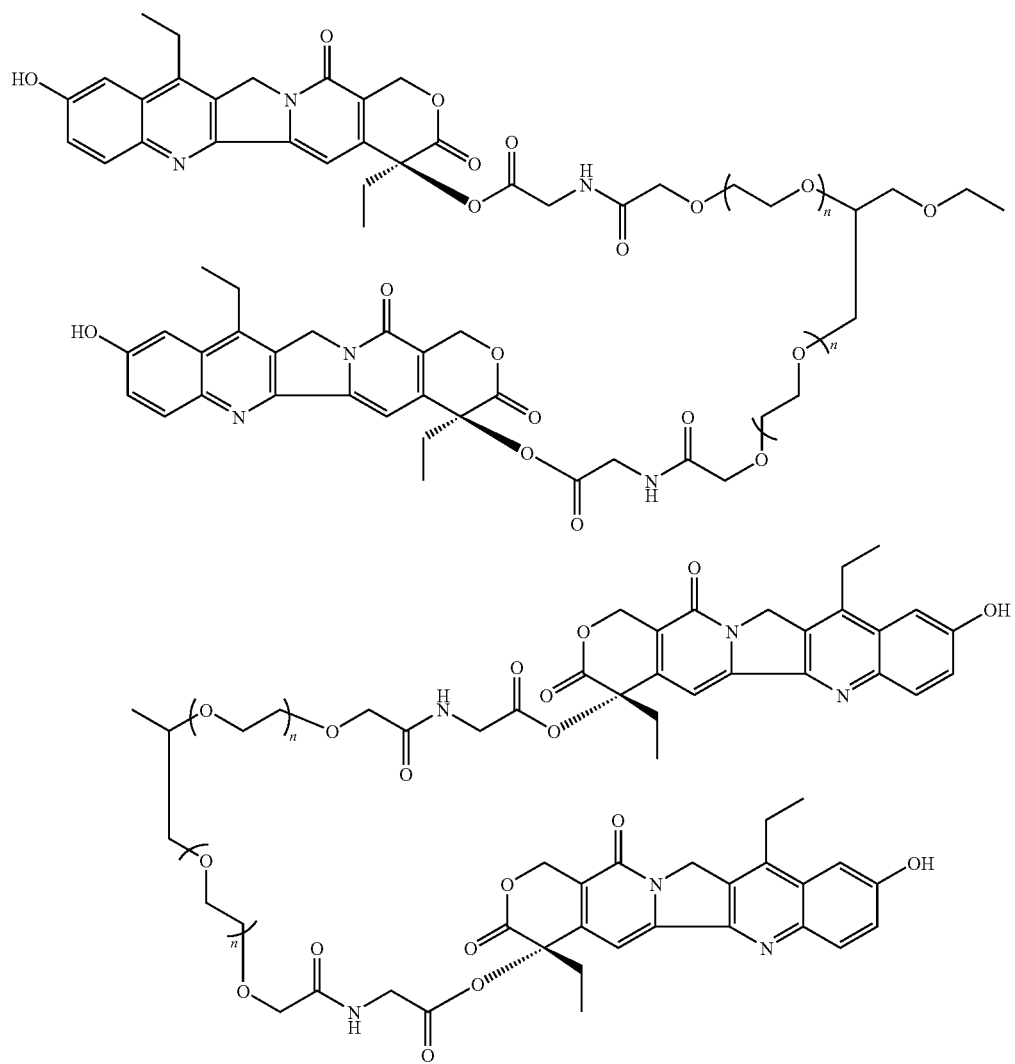

to a mammal in need thereof,
wherein
the effective amount administered is from about 0.3 mg/m² body surface/dose to about 90 mg/m² body surface/dose; and
n is about 227; wherein the non-Hodgkin's lymphoma is a Burkitt's lymphoma or a follicular non-Hodginkin's lymphoma.

18. The method of claim 17 wherein the effective amount administered is from about 0.9 mg/m² body surface/dose to about 30 mg/m² body surface/dose.

19. The method of claim 17, wherein the amount is administered according to a protocol of from about 1 mg/m² body surface/dose to about 16 mg/m² body surface/dose given weekly for three weeks, followed by 1 week without treatment and repeating for about 3 cycles.

20. The method of claim 19, wherein the amount administered per every three weeks is from about 1.25 mg/m² body surface/dose to about 45 mg/m² body surface/dose.

* * * * *